(12) United States Patent
    Manley

(10) Patent No.: US 12,582,733 B2
(45) Date of Patent: Mar. 24, 2026

(54) PARALLEL HEATING SYSTEM AND METHOD FOR AMALGAM LAMPS

(71) Applicant: Tru-D SmartUVC, Memphis, TN (US)

(72) Inventor: Brian Manley, Memphis, TN (US)

(73) Assignee: Tru-D SmartUVC, LLC, Memphis, TN (US)

( * ) Notice: Subject to any disclaimer, the term of this patent is extended or adjusted under 35 U.S.C. 154(b) by 458 days.

(21) Appl. No.: 18/120,420

(22) Filed: Mar. 12, 2023

(65) Prior Publication Data

US 2024/0299603 A1 Sep. 12, 2024

(51) Int. Cl.
    *A61L 2/10* (2006.01)
    *A61L 2/24* (2006.01)
    *H05B 1/02* (2006.01)

(52) U.S. Cl.
    CPC ................. *A61L 2/10* (2013.01); *A61L 2/24* (2013.01); *H05B 1/023* (2013.01); *A61L 2202/11* (2013.01); *A61L 2202/14* (2013.01); *A61L 2202/16* (2013.01); *A61L 2202/25* (2013.01); *H05B 2203/007* (2013.01)

(58) Field of Classification Search
    CPC .............. A61L 2/10; A61L 2/24; H05B 1/023
    See application file for complete search history.

(56) References Cited

U.S. PATENT DOCUMENTS

| | | | |
|---|---|---|---|
| 5,095,336 A | 3/1992 | Corona et al. | |
| 5,891,399 A | 4/1999 | Owesen | |
| 6,656,424 B1 | 12/2003 | Deal | |
| 6,911,177 B2 | 6/2005 | Deal | |
| 7,049,738 B2 | 5/2006 | Fischer et al. | |
| 7,061,173 B2 | 6/2006 | Fischer et al. | |
| 7,095,167 B2 | 8/2006 | Pirovic | |
| 7,175,806 B2 | 2/2007 | Deal et al. | |

(Continued)

FOREIGN PATENT DOCUMENTS

| | | |
|---|---|---|
| CN | 208988634 U | 6/2019 |
| CN | 113332463 A | 9/2021 |

(Continued)

OTHER PUBLICATIONS

International Search Report and Written Opinion for corresponding patent application No. PCT/US2024/019123, dated Jul. 1, 2024, 11 pages.

*Primary Examiner* — Sean E Conley
(74) *Attorney, Agent, or Firm* — Patterson Intellectual Property Law, P.C.; Ryan D. Levy; Gary L. Montle

(57) ABSTRACT

The present disclosure relates to ultraviolet (UV) disinfection devices, systems and methods for automatically preheating a plurality of UV emitters of the UV disinfection device in response to the UV disinfection device being coupled to a power source, independent of the activation of the plurality of EV emitters, or a ballast or power supply thereof, in order to minimize a total disinfection cycle time. In certain optional embodiments, the present disclosure relates to UV disinfection devices, systems and methods for dynamically adjusting a power-level of each of the plurality of UV emitters based on corresponding UV sensor measurements in order to further minimize the total disinfection cycle time. In other optional embodiments, the present disclosure relates to UV disinfection devices, systems and methods for optimizing alignment of each of a plurality of UV emitters within a room in order to further minimize the total disinfection cycle time.

16 Claims, 15 Drawing Sheets

(56)                References Cited

U.S. PATENT DOCUMENTS

| | | | |
|---|---|---|---|
| 7,459,694 | B2 | 12/2008 | Scheir et al. |
| 7,683,542 | B2 | 3/2010 | Voronov et al. |
| 7,816,849 | B2 | 10/2010 | Pirovic |
| 7,829,016 | B2 | 11/2010 | Deal et al. |
| 8,018,130 | B2 | 9/2011 | Van Den Broek et al. |
| 8,067,750 | B2 | 11/2011 | Deal |
| 8,114,342 | B2 | 2/2012 | Jung et al. |
| 8,455,832 | B2 | 6/2013 | Statham et al. |
| 8,564,201 | B2 | 10/2013 | Rooijackers |
| 8,575,567 | B2 | 11/2013 | Lyslo et al. |
| 8,648,530 | B2 | 2/2014 | Schmidt et al. |
| 8,747,753 | B2 | 6/2014 | Engel et al. |
| 8,779,391 | B2 | 7/2014 | Flaherty et al. |
| 8,816,301 | B2 | 8/2014 | Stibich et al. |
| 8,859,994 | B2 | 10/2014 | Deal |
| 8,877,124 | B2 | 11/2014 | Bergman |
| 8,895,939 | B2 | 11/2014 | Lyslo et al. |
| 8,932,535 | B2 | 1/2015 | Hyde et al. |
| 9,023,274 | B2 | 5/2015 | Garner et al. |
| 9,048,083 | B2 | 6/2015 | Voronov |
| 9,095,633 | B1 | 8/2015 | Dayton |
| 9,205,162 | B2 | 12/2015 | Deal et al. |
| 9,272,059 | B2 | 3/2016 | Lyslo et al. |
| 9,345,798 | B2 | 5/2016 | Trapani |
| 9,358,313 | B2 | 6/2016 | Deal |
| 9,468,695 | B2 | 10/2016 | Liao et al. |
| 9,555,143 | B2 | 1/2017 | Deal et al. |
| 9,555,144 | B2 | 1/2017 | Garner et al. |
| 9,592,312 | B2 | 3/2017 | Lyslo et al. |
| 9,597,420 | B2 | 3/2017 | Maxik et al. |
| 9,744,255 | B2 | 8/2017 | Stibich |
| 9,782,505 | B2 | 10/2017 | Lyslo et al. |
| 9,950,088 | B2 | 4/2018 | Garner et al. |
| 10,064,968 | B2 | 9/2018 | Statham et al. |
| 10,092,665 | B2 | 10/2018 | Lyslo et al. |
| 10,195,300 | B2 | 2/2019 | Lloyd |
| 10,245,341 | B2 | 4/2019 | Stibich et al. |
| 10,293,066 | B2 | 5/2019 | Dayton |
| 10,406,254 | B2 | 9/2019 | Garner et al. |
| 10,443,493 | B2 | 10/2019 | Emmerson et al. |
| 10,556,025 | B2 | 2/2020 | Ufkes |
| 10,568,981 | B2 | 2/2020 | Lyslo et al. |
| 10,583,212 | B2 | 3/2020 | Ufkes |
| 10,585,218 | B2 | 3/2020 | Ufkes et al. |
| 10,729,797 | B2 | 8/2020 | Lyslo et al. |
| 10,836,655 | B2 | 11/2020 | Tirn |
| 10,933,149 | B2 | 3/2021 | Lyslo et al. |
| 10,939,517 | B2 | 3/2021 | Glowczwski |
| 10,960,091 | B2 | 3/2021 | Dijkstra et al. |
| 10,967,088 | B2 | 4/2021 | Fudakowski |
| 10,987,440 | B1 | 4/2021 | Sood et al. |
| 11,154,632 | B2 | 10/2021 | Ufkes et al. |
| 11,219,700 | B2 | 1/2022 | Garner et al. |
| 11,253,805 | B1 | 2/2022 | Jones et al. |
| 11,305,031 | B2 | 4/2022 | Sood et al. |
| 11,364,313 | B2 | 6/2022 | Ufkes |
| 11,364,314 | B2 | 6/2022 | Ufkes |
| 11,375,595 | B2 | 6/2022 | Barber et al. |
| 11,382,992 | B2 | 7/2022 | Stibich et al. |
| 11,400,177 | B2 | 8/2022 | Wald et al. |
| 11,439,717 | B1 | 9/2022 | Eggleston |
| 11,511,007 | B2 | 11/2022 | Stibich |
| 11,511,008 | B2 | 11/2022 | Hoang et al. |
| 11,511,423 | B2 | 11/2022 | Vitzrabin et al. |
| 2005/0242013 | A1 | 11/2005 | Hunter et al. |
| 2011/0181187 | A1 | 7/2011 | Voronov et al. |
| 2012/0126134 | A1 | 5/2012 | Deal et al. |
| 2015/0115170 | A1 | 4/2015 | Shostak et al. |
| 2018/0207303 | A1 | 7/2018 | Farren et al. |
| 2020/0338220 | A1 | 10/2020 | Kim |
| 2021/0030909 | A1 | 2/2021 | Mcdonald |
| 2021/0113724 | A1 | 4/2021 | Ufkes et al. |
| 2021/0178000 | A1 | 6/2021 | Lyslo et al. |
| 2021/0290791 | A1 | 9/2021 | Mandaric |
| 2021/0299295 | A1 | 9/2021 | Rubaek et al. |
| 2021/0310637 | A1 | 10/2021 | Yee |
| 2021/0346542 | A1 | 11/2021 | Pan |
| 2021/0353808 | A1 | 11/2021 | Hung et al. |
| 2021/0361799 | A1 | 11/2021 | Gonzalez |
| 2021/0369907 | A1 | 12/2021 | Umenei et al. |
| 2021/0369908 | A1 | 12/2021 | Umenei et al. |
| 2021/0402041 | A1 | 12/2021 | Whinnery et al. |
| 2022/0001069 | A1 | 1/2022 | Allen et al. |
| 2022/0008589 | A1 | 1/2022 | Karitonas |
| 2022/0011746 | A1 | 1/2022 | Jorgenson et al. |
| 2022/0023455 | A1 | 1/2022 | Yates et al. |
| 2022/0023467 | A1 | 1/2022 | Garner et al. |
| 2022/0031897 | A1 | 2/2022 | Saxena et al. |
| 2022/0047761 | A1 | 2/2022 | Lin et al. |
| 2022/0062463 | A1 | 3/2022 | Ramer et al. |
| 2022/0088237 | A1 | 3/2022 | Hauser et al. |
| 2022/0088241 | A1 | 3/2022 | Braverman et al. |
| 2022/0105220 | A1 | 4/2022 | Ufkes et al. |
| 2022/0111086 | A1 | 4/2022 | Childress |
| 2022/0111098 | A1 | 4/2022 | Garner et al. |
| 2022/0125963 | A1 | 4/2022 | Choi et al. |
| 2022/0143249 | A1 | 5/2022 | Pierson et al. |
| 2022/0143250 | A1 | 5/2022 | Pierson et al. |
| 2022/0175987 | A1 | 6/2022 | Cunningham |
| 2022/0184252 | A1 | 6/2022 | Childress et al. |
| 2022/0193281 | A1 | 6/2022 | Dencovski et al. |
| 2022/0226517 | A1 | 7/2022 | Bennett |
| 2022/0257818 | A1 | 8/2022 | Rajasekar et al. |
| 2022/0273836 | A1 | 9/2022 | Frisoli et al. |
| 2022/0288261 | A1 | 9/2022 | Ashdown |
| 2022/0313857 | A1 | 10/2022 | Hunt |
| 2022/0323623 | A1 | 10/2022 | Candelore |
| 2022/0387638 | A1 | 12/2022 | Ufkes et al. |
| 2022/0410050 | A1 | 12/2022 | Jones et al. |
| 2023/0012592 | A1 | 1/2023 | Ufkes |

FOREIGN PATENT DOCUMENTS

| | | | |
|---|---|---|---|
| EP | 2928506 | B1 | 9/2017 |
| EP | 3892307 | A1 | 10/2021 |
| WO | 2011055140 | A1 | 5/2011 |
| WO | 2013037440 | A1 | 3/2013 |

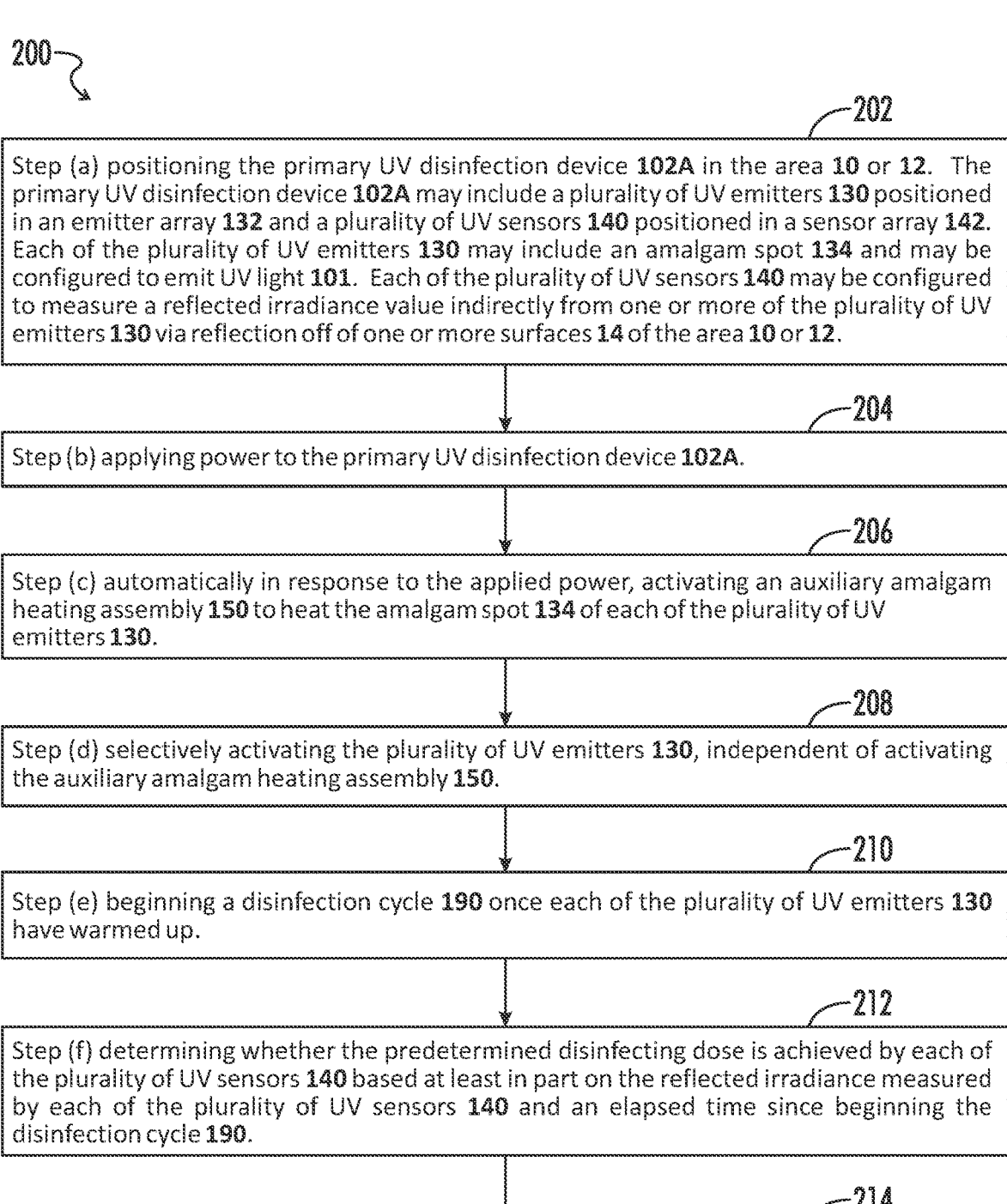

200

202

Step (a) positioning the primary UV disinfection device 102A in the area 10 or 12. The primary UV disinfection device 102A may include a plurality of UV emitters 130 positioned in an emitter array 132 and a plurality of UV sensors 140 positioned in a sensor array 142. Each of the plurality of UV emitters 130 may include an amalgam spot 134 and may be configured to emit UV light 101. Each of the plurality of UV sensors 140 may be configured to measure a reflected irradiance value indirectly from one or more of the plurality of UV emitters 130 via reflection off of one or more surfaces 14 of the area 10 or 12.

204

Step (b) applying power to the primary UV disinfection device 102A.

206

Step (c) automatically in response to the applied power, activating an auxiliary amalgam heating assembly 150 to heat the amalgam spot 134 of each of the plurality of UV emitters 130.

208

Step (d) selectively activating the plurality of UV emitters 130, independent of activating the auxiliary amalgam heating assembly 150.

210

Step (e) beginning a disinfection cycle 190 once each of the plurality of UV emitters 130 have warmed up.

212

Step (f) determining whether the predetermined disinfecting dose is achieved by each of the plurality of UV sensors 140 based at least in part on the reflected irradiance measured by each of the plurality of UV sensors 140 and an elapsed time since beginning the disinfection cycle 190.

214

Step (g) completing the disinfection cycle 190 and deactivating the auxiliary amalgam heating assembly 150 once each of the plurality of UV sensors 140 has achieved the predetermined disinfecting dose.

*FIG. 7*

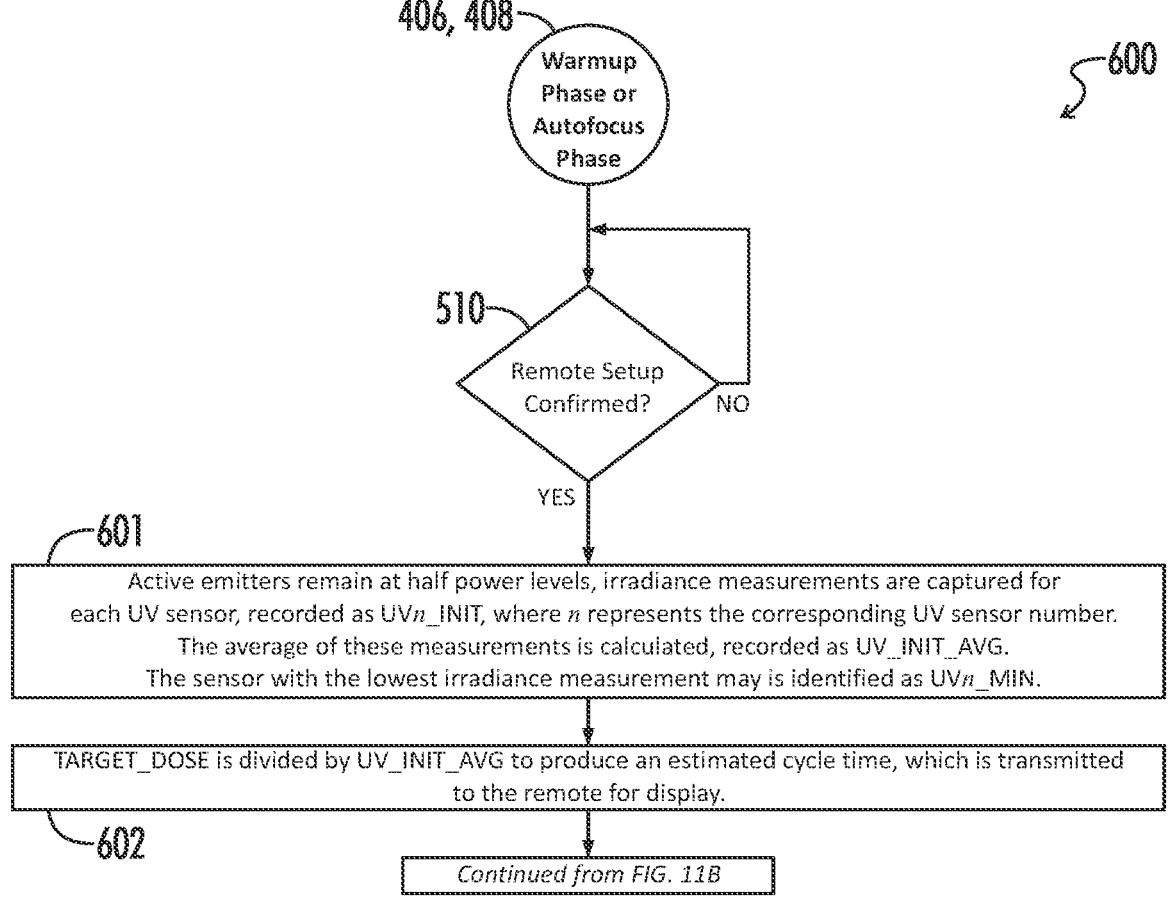

406, 408

Warmup Phase or Autofocus Phase

600

510

Remote Setup Confirmed? — NO

YES

601

Active emitters remain at half power levels, irradiance measurements are captured for each UV sensor, recorded as $UVn\_INIT$, where $n$ represents the corresponding UV sensor number. The average of these measurements is calculated, recorded as $UV\_INIT\_AVG$. The sensor with the lowest irradiance measurement may is identified as $UVn\_MIN$.

TARGET_DOSE is divided by UV_INIT_AVG to produce an estimated cycle time, which is transmitted to the remote for display.

602

Continued from FIG. 11B

*FIG. 11A*

PARALLEL HEATING SYSTEM AND METHOD FOR AMALGAM LAMPS

A portion of the disclosure of this patent document contains material that is subject to copyright protection. The copyright owner has no objection to the reproduction of the patent document or the patent disclosure as it appears in the U.S. Patent and Trademark Office patent file or records, but otherwise reserves all copyright rights whatsoever.

FIELD OF THE INVENTION

The present disclosure relates generally to methods, systems, and devices for bacterial, fungal, and/or viral sterilization and disinfection. More particularly, the present disclosure pertains to methods, systems, and devices for sterilizing and disinfecting rooms and similar enclosed areas using radiant energy emission.

BACKGROUND

Healthcare-Associated Infections (HAIs) are common, costly, and sometimes lethal. In American hospitals alone, the Centers for Disease Control (CDC) estimates that HAIs account for an estimated 1.7 million infections and 99,000 associated deaths each year. The nature of bacteria acquired in the hospital setting differs significantly from bacteria found in a community setting primarily in their resistance to antibiotic therapy.

Attempts to eradicate surface contaminants from the hospital setting have varied greatly in strategy and success. These have ranged from antiseptic soaps to fumigation with formaldehyde gas. Recently, ultraviolet (UV) sterilization devices have been developed and are being temporarily deployed to sterilize and disinfect entire rooms. Sterilization and/or disinfection of surfaces can be accomplished by illuminating or irradiating surfaces with radiant energy, such as from a UV emitting source. These types of UV disinfection (or sterilization) devices generally utilize low to medium pressure mercury lamps. More recently, amalgam lamps are being utilized as they provide up to ten times the UV power density of conventional low-pressure mercury lamps and can even be used at high ambient temperatures of up to 90° C.

One of the major issues associated with these types of UV disinfection devices is the amount of time it takes the device to complete a disinfection process once deployed, also known as the total disinfection cycle time (or cycle time). Competitive device manufacturers in this space continually highlight the cycle time as a distinguishing factor and advantage over competitors. Amalgam lamps, for example, take 3 to 5 minutes (or sometimes more) to reach peak UV output. One way to reduce cycle time is to reduce the warm-up time (or period) of the lamps. The device warm-up time may also be cited by competitive device manufactures as unnecessarily increasing the total disinfection cycle time as the actual administration of UV irradiance cannot be accurately measured until the lamps are warmed up to their constant operating state.

The most prevalent existing method of decreasing the warm-up period involves lamp filament (or cathode) "pre-heating". This circuitry is commonly integrated in many fluorescent ballasts as this method is also used to extend the useful life of lamps by avoiding the damaging effects of cold/instant ignition, wherein full power is immediately applied to lamp filaments. This method of filament pre-heating is controlled by the ballast and, accordingly, cannot be activated until power is applied to the ballast. Accordingly, improving or reducing warm-up time using this method is for the most part only achieved through ballast and/or lamp selection. This severely limits the range of options for system designers. While this technology is useful for the sake of extending lamp life, its impact to warm-up time reduction is considered insufficient for amalgam type lamps as filament pre-heating does not increase the amalgam temperature of the lamp.

In summary, the disadvantage of presently know methods of accomplishing a decreased warm-up period are at least two-fold: first, warm-up may only begin when the ballast circuit is activated, and second, the element being pre-heated has very limited impact on amalgam temperature.

BRIEF SUMMARY

In view of at least some of the above-referenced problems in conventional UV disinfection device lamp preheating methods an exemplary object of the present disclosure may be to provide an auxiliary amalgam heating assembly, system, and method configured to reduce the total disinfection cycle time. An exemplary such assembly may desirably function independently of the lamp and/or ballast, thereby being capable of activating and achieving optimal amalgam temperatures even while a lamp and ballast are inactive. As such, the assembly, system, and method, as disclosed herein, may hold lamps within an optimal temperature range before activation to nearly eliminate the warm-up period. The independence of operation allows the system designer to be agnostic with regards to amalgam lamp and ballast selection, whereas prior art dictates that warm-up properties are a direct result of lamp and ballast selection.

The primary advantage with this approach is recognizing that an unknown period of time will always exist between the time a user intends to activate a UV disinfection device/ process and the time at which the disinfection process actually begins. This period of time can vary but is useful in beginning the warm-up process via the auxiliary amalgam heating assembly.

Upon plugging-in the UV disinfection device or otherwise beginning the operation procedure from the device's control interface, the system is aware that a disinfection process and lamp activation is imminent. During this time, the amalgam will be pre-heated via a direct conduction method without activation of the ballast circuitry. As a result, when the ballast and lamp are finally activated, the amalgam will have achieved its proper operating temperature without reliance on filament pre-heating and/or the self-heating effects inherent with an activated low pressure mercury vapor lamp, which is generally associated with the lamps typical long warm-up time.

The exemplary such assembly, system, and method may further reduce the total disinfection cycle time via the implementation of one or more of an autofocus phase and/or a dynamic dosing phase by a UV disinfection device. The autofocus phase may desirably rotate the emitter and sensor array of the device to capture reflected irradiance measurements at each UV sensor in at least two array positions. By obtaining measurements in multiple positions, reflected irradiance will be captured with high resolution over a 360° field of view. The system may then compare the irradiance measurements captured by each UV sensor in each array position, returning the emitter and sensor array to an optimal position for completing the disinfection cycle.

The dynamic dosing phase may desirably vary the power-level of active emitters of the device. While emitter power is varied, the system analyses the resulting impact to measured reflected irradiance values at each UV sensor. The cycle time impact of each UV sensor is determined, relative to measured irradiance values, and the system determines the appropriate order in which each of the UV sensors will be targeted to achieve the required disinfecting dose. Sensors which measure the lowest levels of reflected irradiance during the analysis period will be targeted to achieve the required dose first, while sensors measuring a higher level of reflected irradiance will be targeted last. As a result, varying emitter power to maximize the measured irradiance of each UV sensor, in order from lowest initial value to highest initial value, the system may achieve the fastest allowable total disinfection cycle time utilizing the limited power available from a standard wall outlet.

BRIEF DESCRIPTION OF THE SEVERAL VIEWS OF THE DRAWINGS

FIG. 7 is a flowchart of a method of disinfecting an area with a predetermined disinfection dose of UV energy in accordance with the present disclosure.

FIG. 11A is a flowchart containing additional optional dynamic dosing details of the method shown in the flowchart of FIG. 9 in accordance with the present disclosure.

DETAILED DESCRIPTION

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

The words "connected", "attached", "joined", "mounted", "fastened", and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Unless specifically stated otherwise, any part of the apparatus of the present disclosure may be made of any appropriate or suitable material including, but not limited to, metal, alloy, polymer, polymer mixture, wood, composite, or any combination thereof.

Figure 1A:
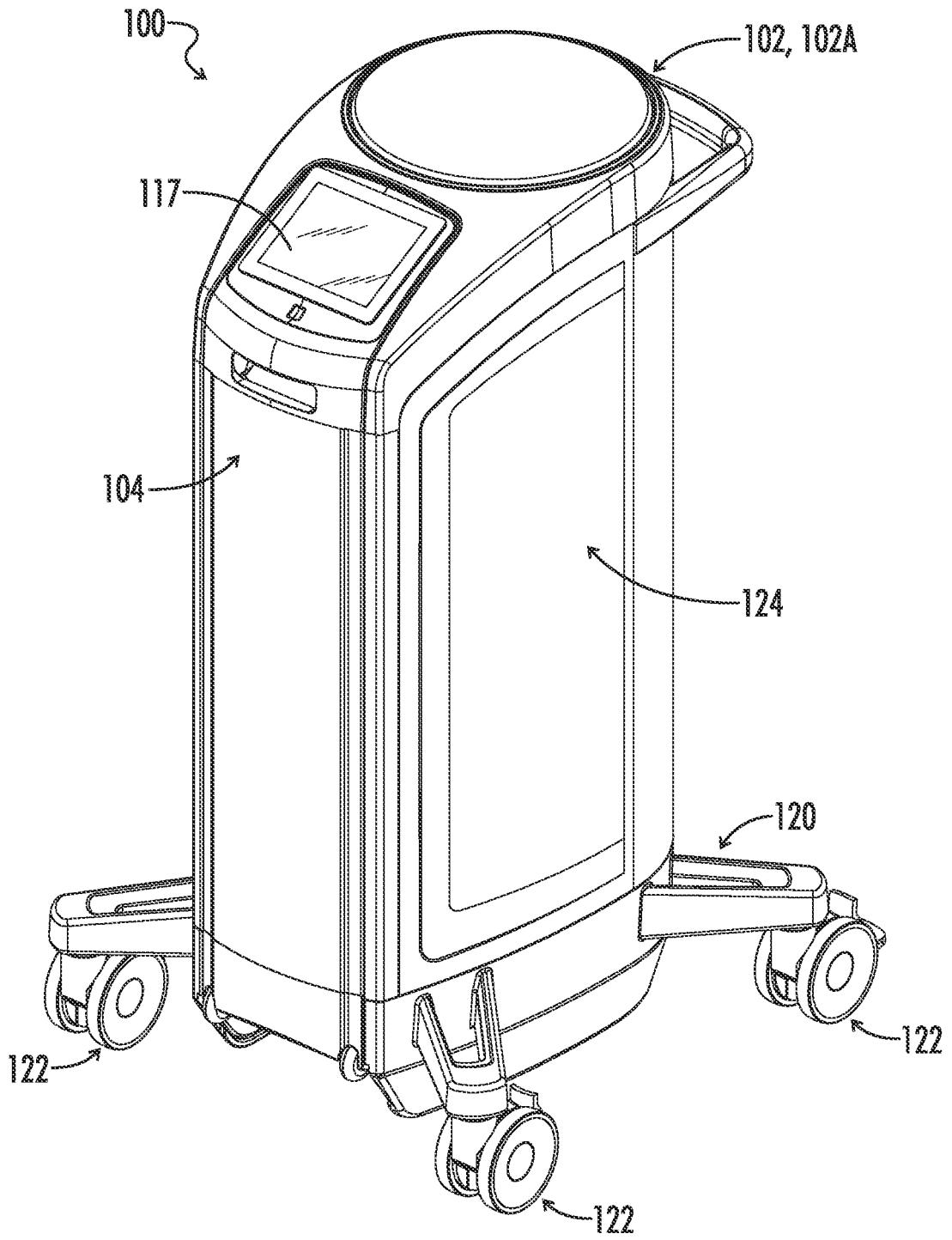
FIG. 1A is a perspective view of an ultraviolet (UV) disinfection system in accordance with the present disclosure.
Figure 1B:
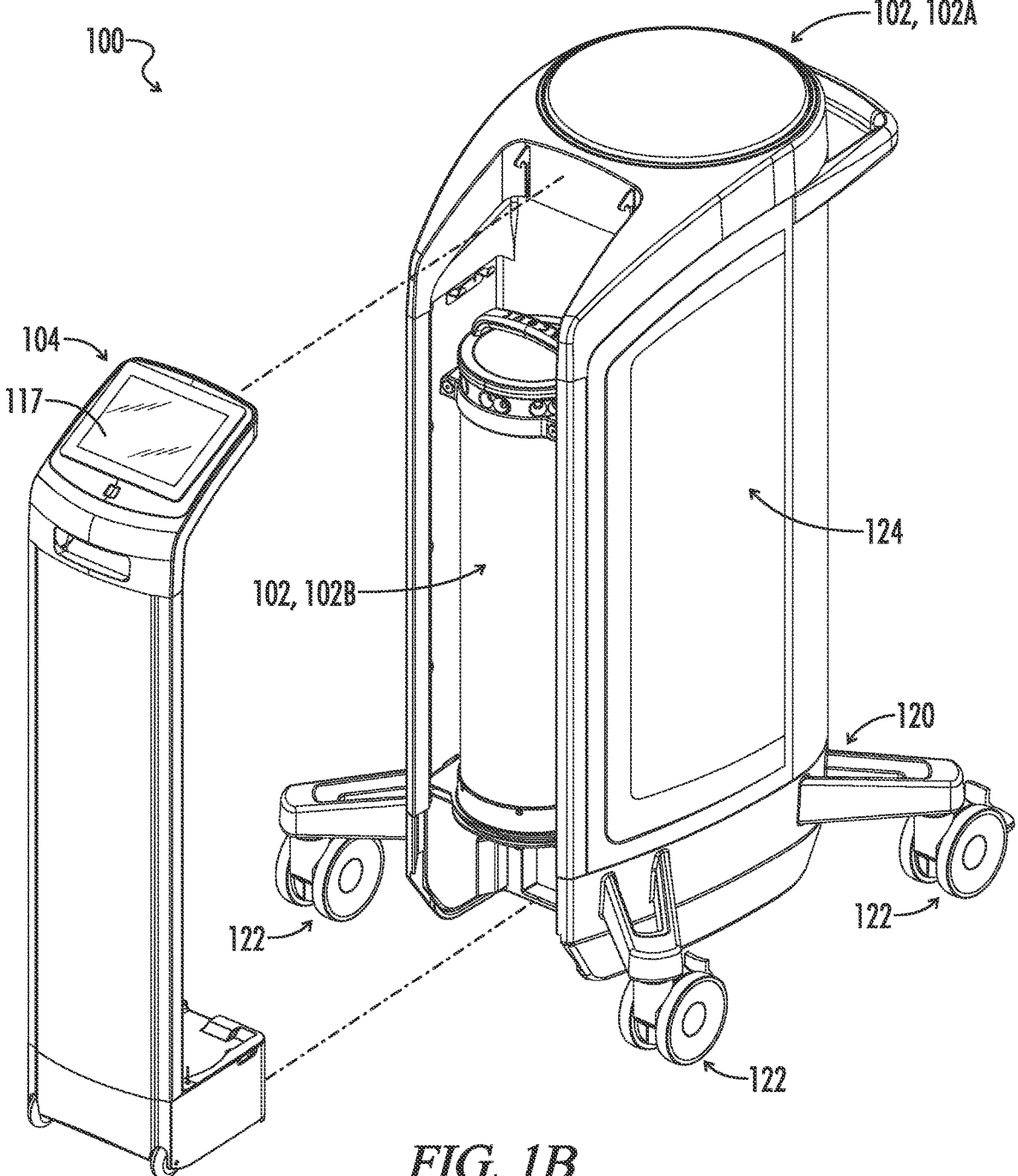
FIG. 1B is a partially exploded perspective view of the UV disinfection system of FIG. 1A in accordance with the present disclosure.
Figure 1C:
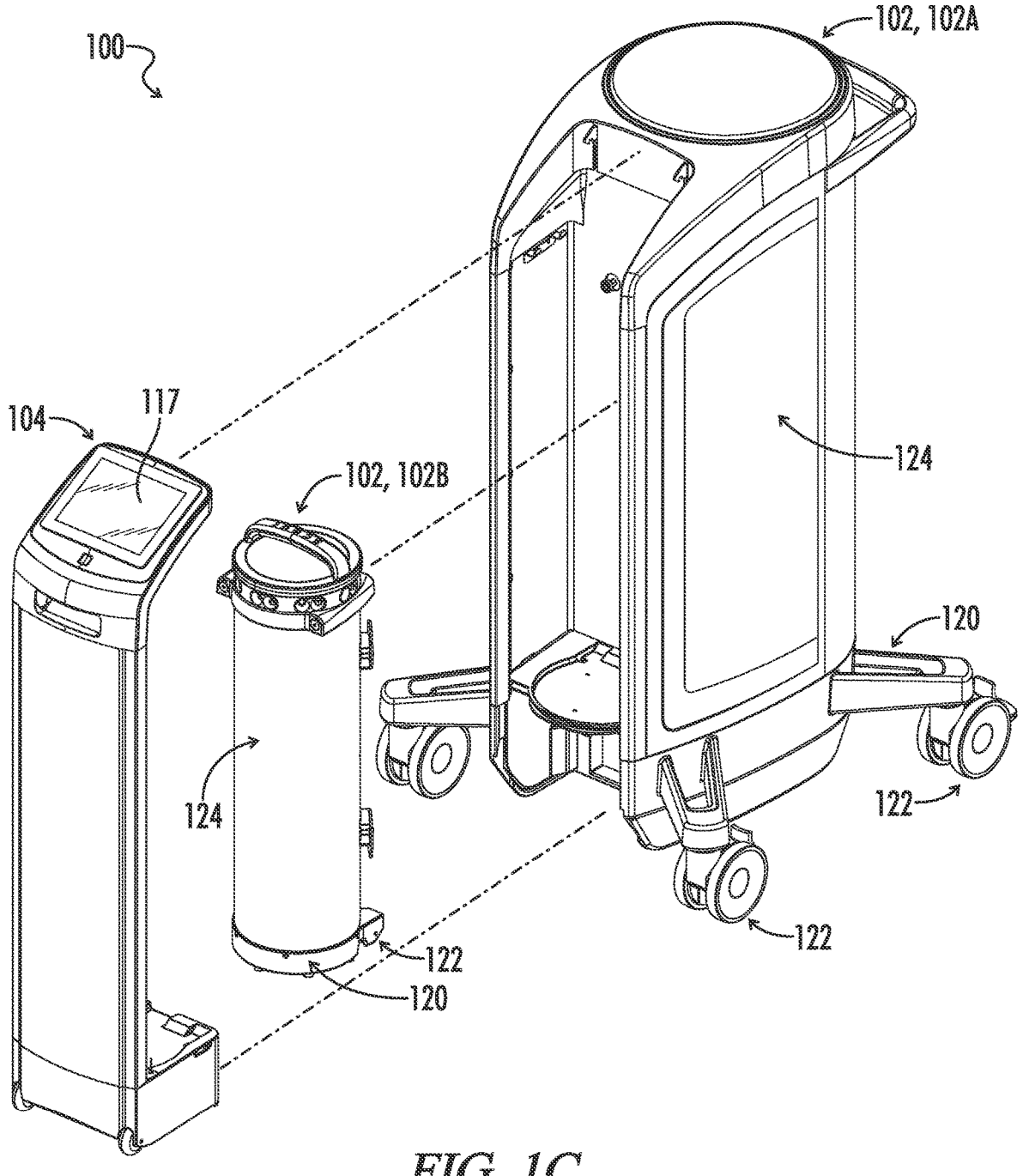
FIG. 1C is an exploded perspective view of the UV disinfection system of FIG. 1A in accordance with the present disclosure.
Figure 2:
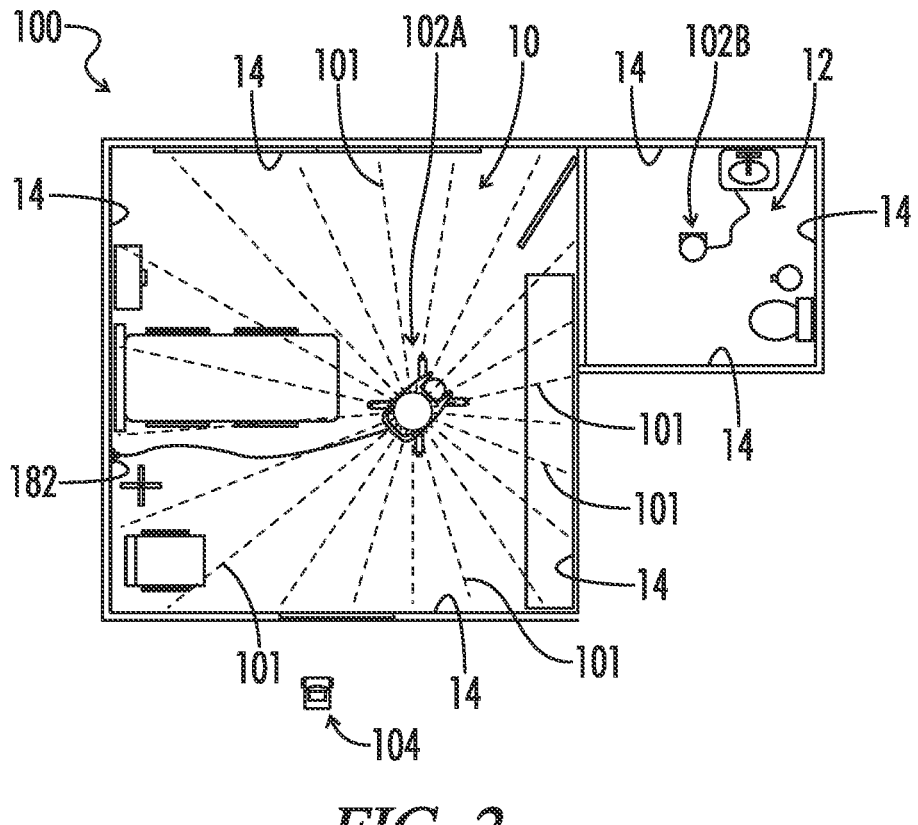
FIG. 2 is an upper perspective view of the UV disinfection system of FIG. 1A with primary and auxiliary UV disinfection devices thereof deployed in different areas in accordance with the present disclosure.
Figure 3A:
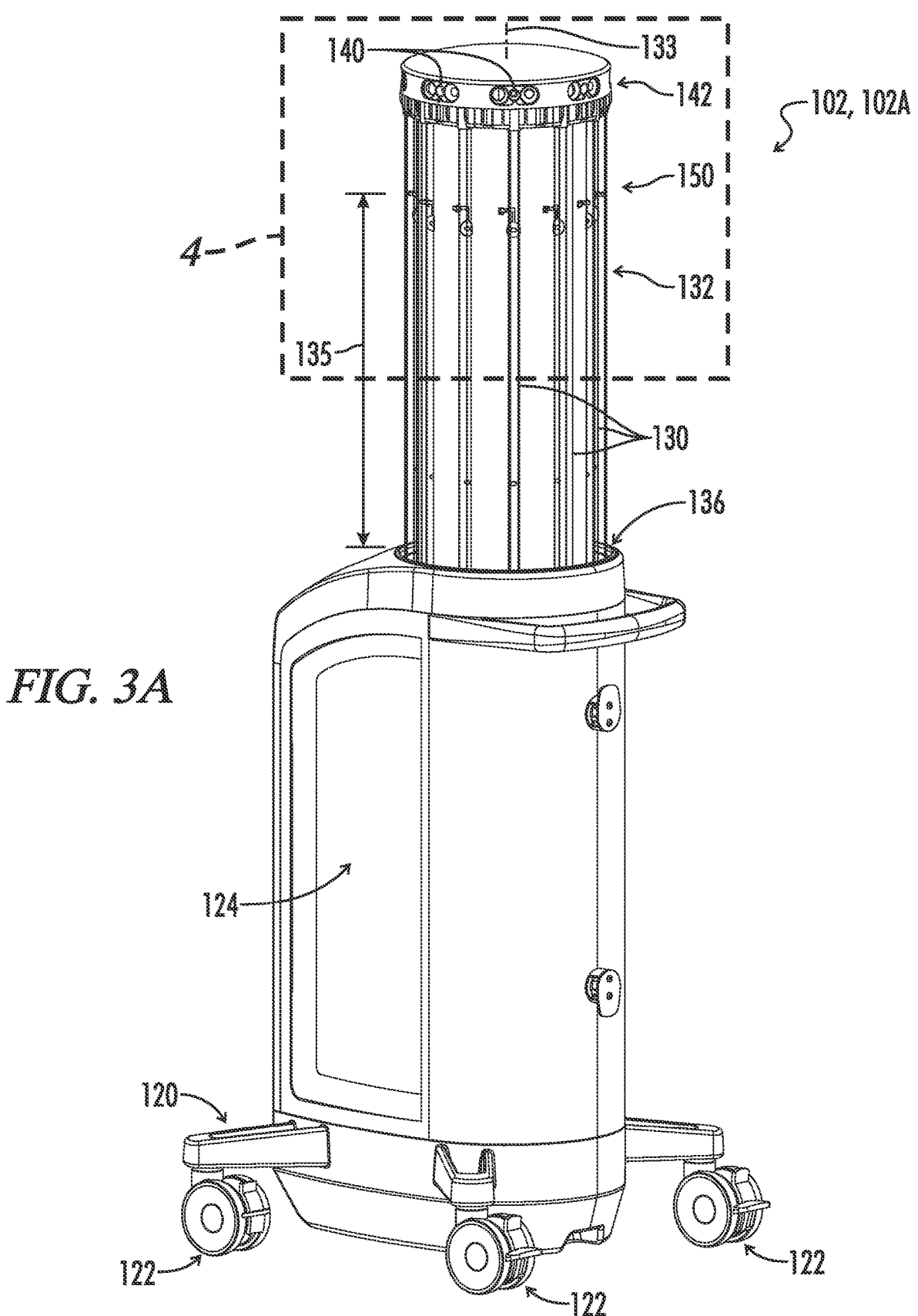
FIG. 3A is a perspective view of the primary UV disinfection device of the UV disinfection system of FIG. 1A with UV emitters of the device in a deployed position in accordance with the present disclosure.
Figure 3B:
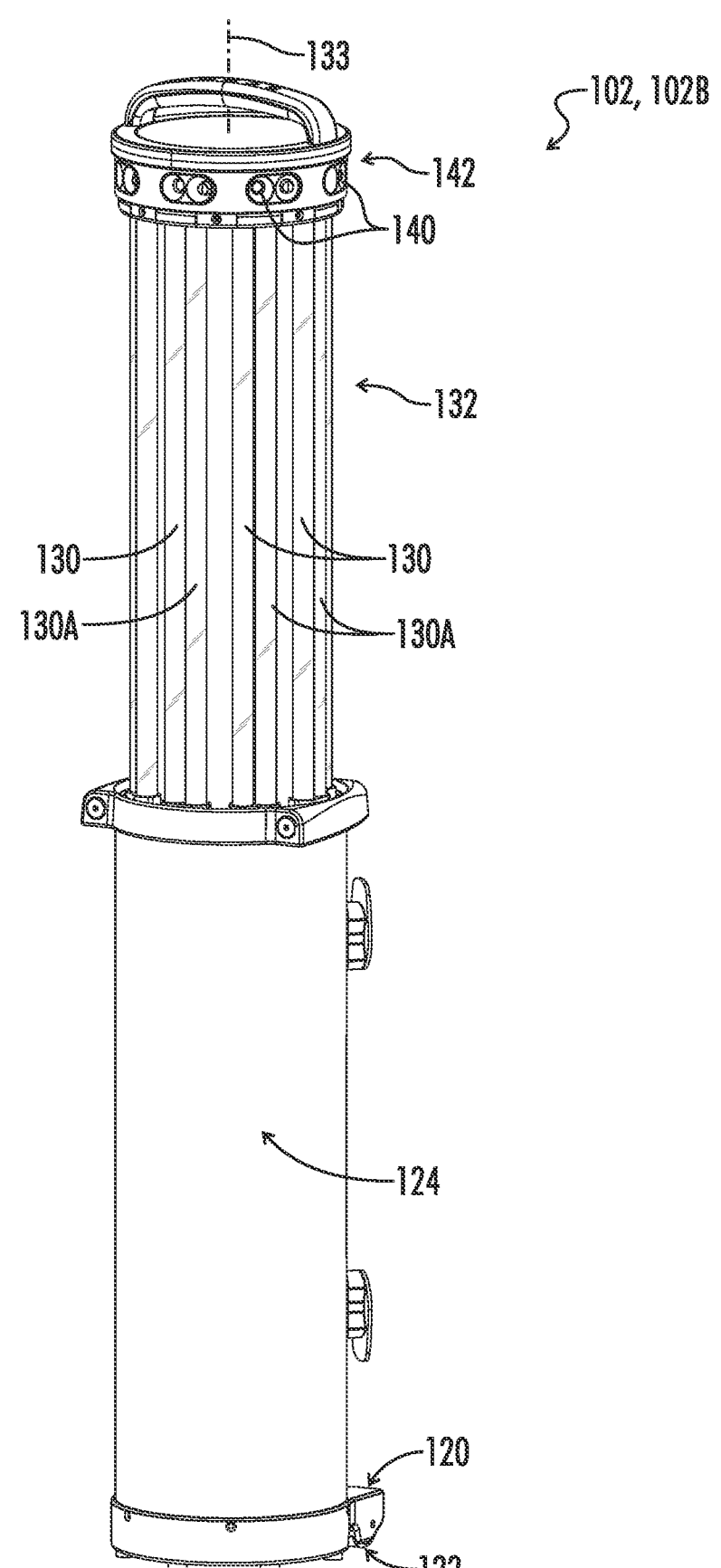
FIG. 3B is a perspective view of the auxiliary UV disinfection device of the UV disinfection system of FIG. 1C with UV emitters of the device in a deployed position in accordance with the present disclosure.

Referring to FIGS. 1A-3B, various embodiments of a disinfection system 100 for irradiating an area 10 or 12 (as illustrated in FIG. 2) with ultraviolet (UV) light are illustrated. The disinfection system 100 may include one or more UV disinfection devices 102 and a mobile control unit 104 configured to be positioned safely outside of the area 10 or 12. The mobile control unit 104 may be configured to remotely control the one or more UV disinfection devices 102.

As illustrated in FIG. 1A, the one or more UV disinfection devices 102 of the disinfection system 100 may include a primary UV disinfection device 102A. The primary UV disinfection device 102A may also be referred to herein as a UV disinfection device 102A. The primary UV disinfection device 102A may be configured to carry the mobile control unit 104. The mobile control unit 104 may be configured to dock with and may even be charged by the primary UV disinfection device 102A. As illustrated in FIG. 1B, the one or more UV disinfection devices 102 of the disinfection system 100 may include an auxiliary UV disinfection device 102B. The auxiliary UV disinfection device 102B may be configured to be carried by the primary UV disinfection device 102A. The auxiliary UV disinfection device 102B may also be configured to dock with and may even be charged by the primary UV disinfection device 102A. As illustrated by FIG. 1C, each of the mobile control unit 104 and the auxiliary UV disinfection device 102B are exploded (or separated) from the primary UV disinfection device 102A.

As illustrated in FIG. 2, the disinfection system 100 may utilize the one or more UV disinfection devices 102 to disinfect one or more associated areas 10, 12 with UV light 101. The UV light 101 may also be referred to herein as UV energy 101. The auxiliary UV disinfection device 102B may be useful for cleaning small areas 12 (e.g., bathrooms or the like) while the primary UV disinfection device 102A may be more useful for cleaning large areas 10 (e.g., a patient's room, an operating room, or the like).

As disclosed herein, the auxiliary UV disinfection device 102B may be a scaled down version of the primary UV disinfection device 102A. Accordingly, elements of each of the primary UV disinfection device 102A and the auxiliary UV disinfection device 102B may be numbered and function similarly. As such, the following disclosures reference to the one or more UV disinfection devices 102 may be equally applicable to each of the primary UV disinfection device 102A and the auxiliary UV disinfection device 102B.

The one or more UV disinfection devices 102 may include a mobile base 120. The mobile base 120 may include one or more ground engaging units 122 which may be configured to support the one or more UV disinfection devices 102 and enable the mobility thereof.

As illustrated in FIGS. 3A-5, the one or more UV disinfection devices 102 may further include a plurality of UV emitters 130 and a plurality of UV sensors 140 configured to telescope upward from within a housing 124 of the one or more UV disinfection devices 102 coupled to the mobile base 120. The plurality of UV emitters 130 may also be referred to herein as a plurality of UV lamps 130. Each of the plurality of UV emitters 130 may be tube-like, oriented vertically, and configured to emit UV light 101 (as illustrated in FIG. 2). Further, the plurality of UV emitters 130 may be positioned in an emitter array 132. The emitter array 132 may also be referred to herein as a circumferential emitter array 132. In certain optional embodiments, each of the plurality of UV emitters 130 may be associated with at least one of the plurality of UV sensors 140. In other embodiments, each of the plurality of UV emitters 130 may be vertically aligned with at least one of the plurality of UV sensors 140.

The plurality of UV sensors 140 may be positioned in a sensor array 142. The sensor array 142 may also be referred to herein as circumferential sensor array 142. In certain optional embodiments, the emitter array 132 and the sensor array 142 may be rigidly coupled together and generally referred to as an array. In other optional embodiments, each of the emitter array 132 and the sensor array 142 may be configured to rotate independently of each other.

The plurality of UV sensors 140 may be configured to generate reflected irradiance data 144 corresponding to a measured reflected irradiance value by each of the plurality of UV sensors 140. Each of the plurality of UV sensors 140 may be narrowly focused and configured to measure only reflected irradiance so as to exclude measuring direct radiant energy from each of the plurality of UV emitters 130. Accordingly, each of the plurality of UV sensors 140 is configured to only measure the radiant energy as reflected (e.g., reflected irradiant energy) from a specific point of one of the one or more surfaces 14 of the area 10 or 12. The reflected irradiance data 144 may include: (1) a plurality of initial reflected irradiance values measured by each of the plurality of UV sensors 140 and corresponding to a plurality of array positions of the circumferential sensor array 142 (wherein the plurality of array positions may be rotationally offset from each other), (2) optimal position initial reflected irradiance values measured by the plurality of UV sensors 140 corresponding to an optimal array position, (3) real-time reflected irradiance values measured before, during, or after the power-level of each of the plurality of UV emitters 130 is dynamically adjusted, or (4) the like.

Each of the plurality of UV emitters 130 may be any type of lamp or bulb configured to emit UVC energy, such as, for example, a low-pressure mercury lamp, an amalgam lamp, or the like. Each of the plurality of UV emitters 130 may be adjustable (e.g., dimmable) based upon a power-level supplied to each of the plurality of UV emitters 130. The power-level supplied to each of the plurality of UV emitters 130 may be at least partially controlled by at least one ballast 138. The at least one ballast 138 may also be referred to herein as at least one power supply 138.

Figure 4:
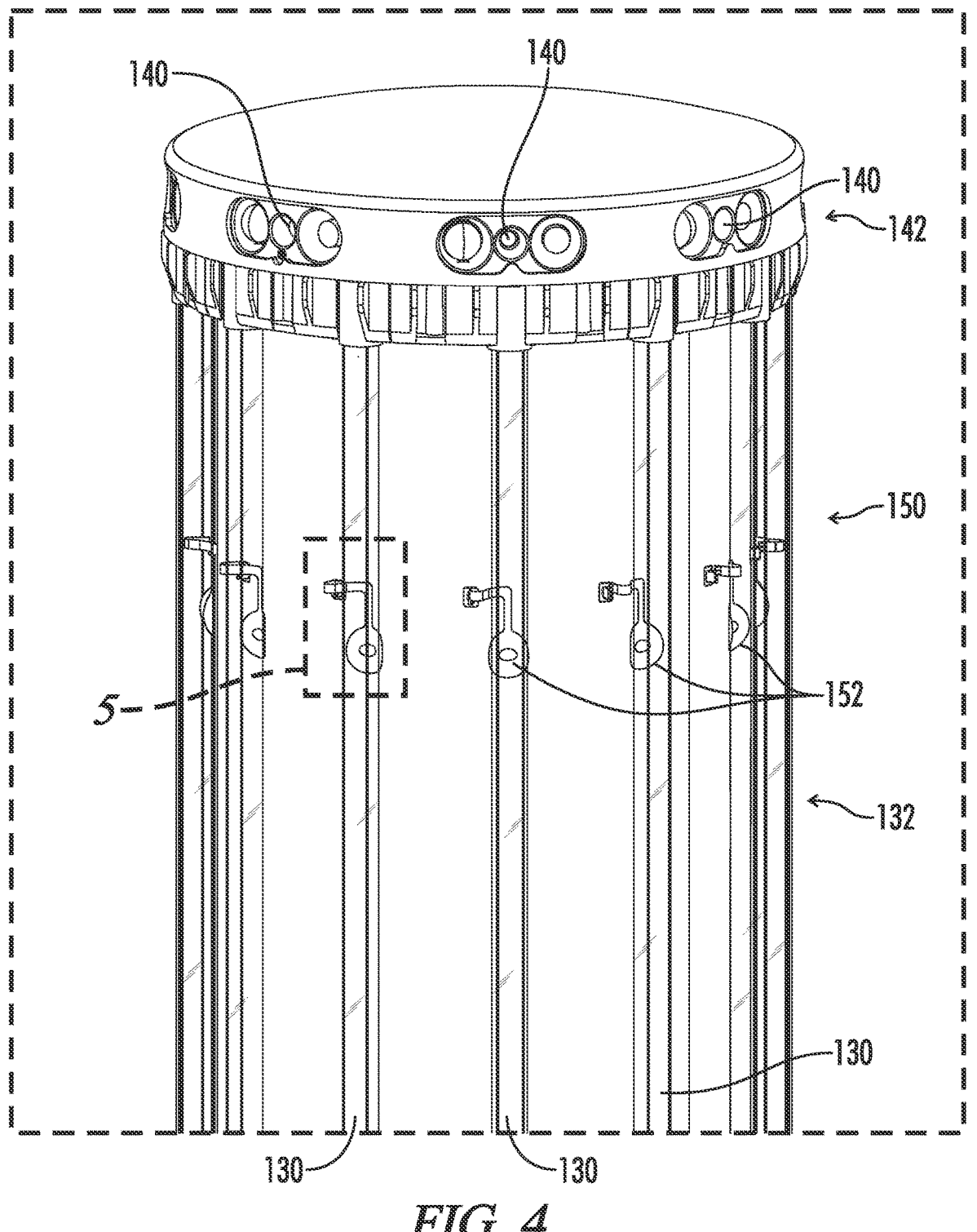
FIG. 4 is an enlarged perspective view of the primary UV disinfection device of FIG. 3A taken of area 4 of FIG. 3A in accordance with the present disclosure.
Figure 5:
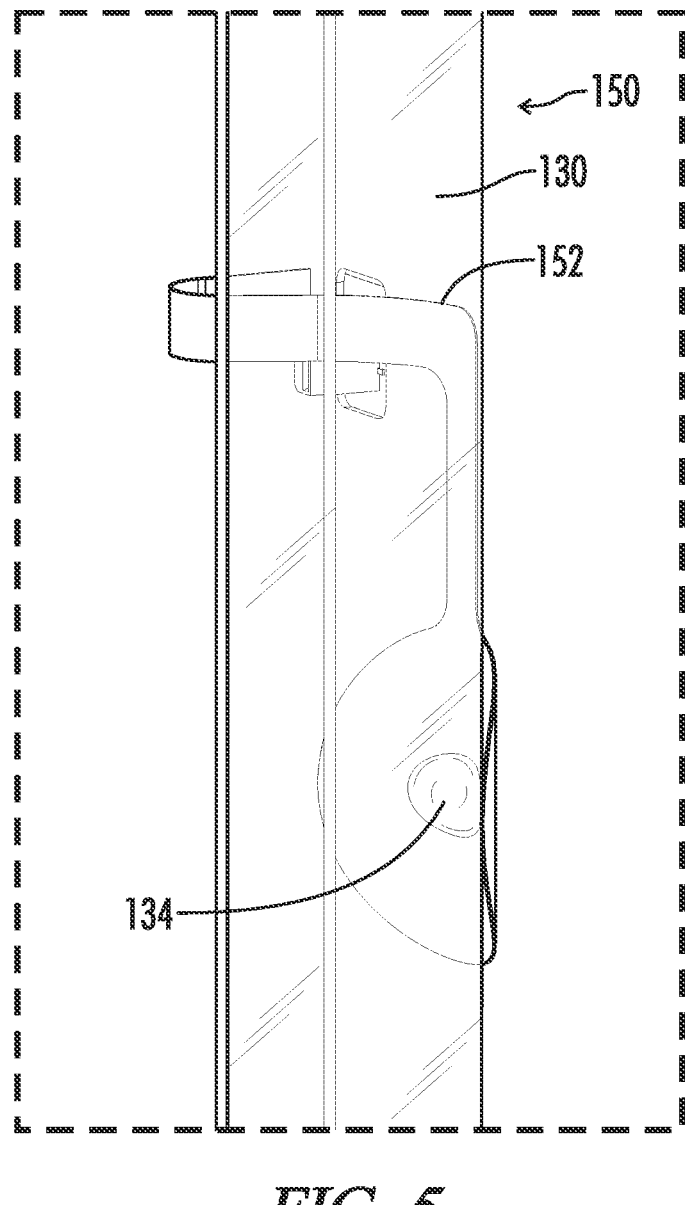
FIG. 5 is an enlarged perspective view of the primary UV disinfection device of FIG. 3A taken of area 5 of FIG. 4 in accordance with the present disclosure.

As illustrated in FIGS. 4-5, each of the plurality of UV emitters 130 may be an amalgam lamp having an amalgam spot 134 coupled to an interior surface of the lamp. The amalgam spot 134 may also be referred to herein as an interior amalgam spot 134. The amalgam spot 134 of each of the plurality of UV emitters 130 may be positioned at a common height 135 relative to a lower end 136 of each of the plurality of UV emitters 130. The common height 135 may also be referred to herein as a predetermined common distance 135. In certain optional embodiments, the amalgam spot 134 of each of the plurality of UV emitters 130 may be positioned such that they are proximate to a central axis 133 of the emitter array 132. In other words, each of the plurality of UV emitters 130 may be rotated such that the amalgam spot 134 of each of the plurality of UV emitters 130 is as close as possible to the central axis 133.

As illustrated in FIGS. 4-5, the primary UV disinfection device 102A may include an auxiliary amalgam heating assembly 150 configured to preheat the amalgam spot 134 of each of the plurality of UV emitters 130, which may reduce the warmup time of each of the plurality of UV emitters 130. In certain optional embodiments (not shown), the auxiliary UV disinfection devices 102B may also include an auxiliary amalgam heating assembly. The auxiliary amalgam heating assembly 150 may also be referred to herein as a flux accelerator assembly 150 or a flux accelerator apparatus 150. The auxiliary amalgam heating assembly 150 may include a plurality of heating elements 152. Each of the plurality of heating elements 152 may be positioned proximate to the amalgam spot 134 of each of the plurality of UV emitters 130. The auxiliary amalgam heating assembly 150 may be configured to activate in response to a power state of the one or more UV disinfection devices 102 (e.g., the primary UV disinfection device 102A).

The power state of each of the one or more UV disinfection devices 102 may correspond to whether the device is coupled to an external power source 182, such as, for example, AC power. In certain optional embodiments, the power state may also or alternatively correspond to whether the one or more UV disinfection devices 102 is in an on state or an off state.

Figure 6:
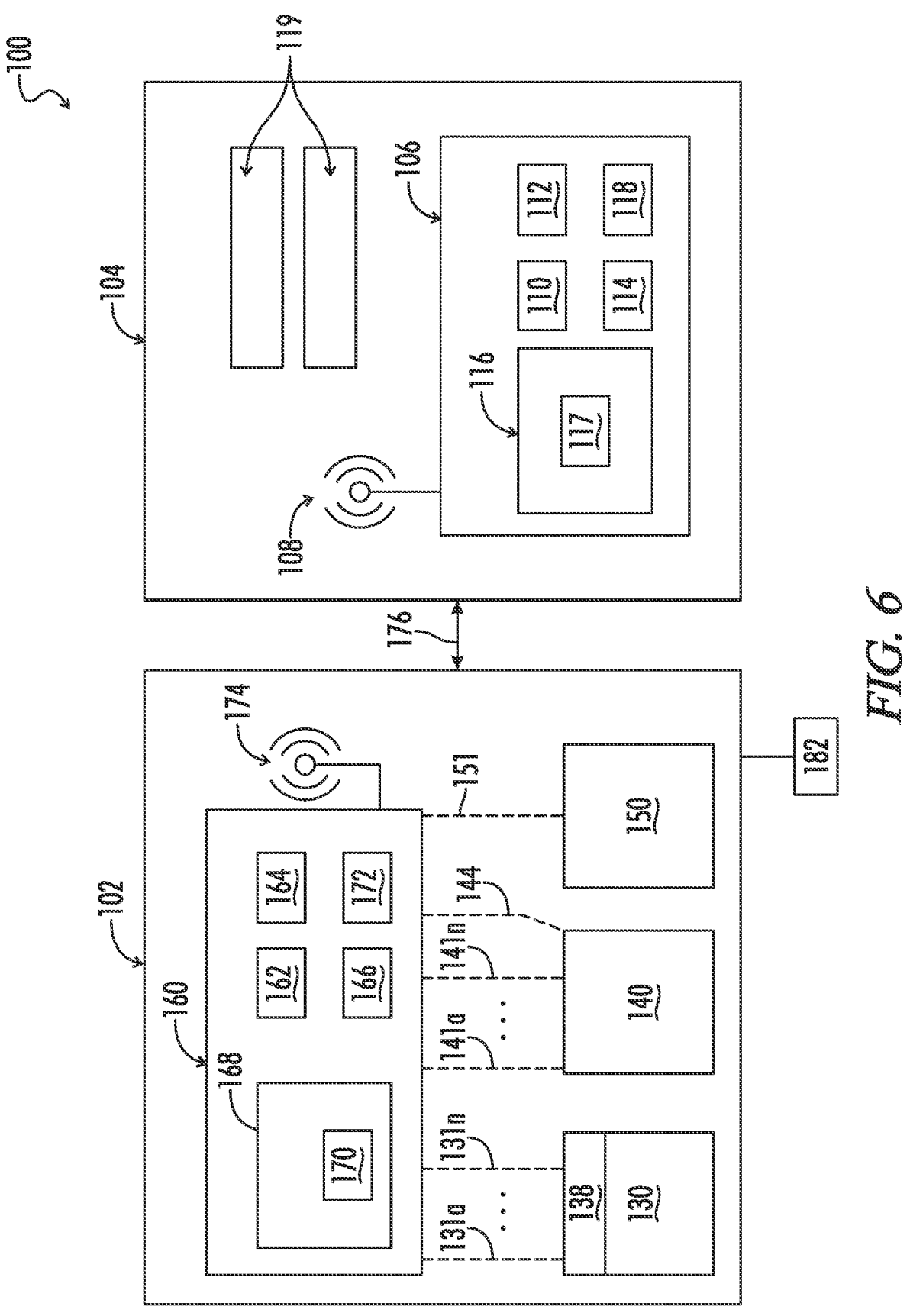
FIG. 6 is a block diagram of an exemplary control system of the UV disinfection system of FIG. 1A in accordance with the present disclosure.

Referring to FIG. 6, an exemplary control system of the disinfection system 100 is schematically illustrated. The one or more UV disinfection devices 102 may include a single controller 160 or discrete controllers for each of at least the plurality of UV emitters 130, the plurality of UV sensors 140, and optionally an auxiliary amalgam heating assembly 150. Similarly, the mobile control unit 104 may include a single controller 106 or discrete controllers for controlling at least one of the primary UV disinfection device 102A and the auxiliary UV disinfection device 102B.

The controller 160 of the one or more UV disinfection devices 102 may include a processor 162, a computer readable memory medium 164, a database 166, and an input/output module or control panel 168 having a display 170. Likewise, the controller 106 of the mobile control unit 104 may include a processor 110, a computer readable memory medium 112, a database 114, and an input/output module or control panel 116 having a display 117.

As illustrated, the controller 160 of the one or more UV disinfection devices 102 may be configured to receive reflected irradiance data 144 from each of the plurality of UV sensors 140. The controller 160 may also receive various other inputs from internal and external sources regarding other operating parameters of the one or more UV disinfection devices 102, such as, for example, whether movement is sensed within the area 10 or 12, whether a door to the area 10 or 12 is secured, or the like. In other optional embodiments (not shown), the controller 106 of the mobile control unit 104 may be configured to receive this same data remotely from the one or more UV disinfection devices 102, for example, using a wireless transceiver 108 coupled to the controller 106 and a wireless transceiver 174 coupled to the controller 160. Each of the wireless transceivers 108, 174 may be configured to utilize radio frequency (RF), Bluetooth, Bluetooth Low Energy, WiFi, cellular, pulse light, or the like, to send and receive data 176.

Based upon various operational parameters which may be defined by the computer programming product 172, the controller 160 may generate various control signals which may be communicated to each of the plurality of UV emitters 130 (schematically illustrated via the dashed communication lines 131a-n, where n is the number of UV emitters), each of the plurality of UV sensors 140 (schematically illustrated via the dashed communication lines 141a-n, where n is the number of UV sensors), and the auxiliary amalgam heating assembly 150 (schematically illustrated via the dashed communication line 151). In certain optional embodiments, based upon various operational parameters which may be defined by the computer programming product 118, the controller 106 may generate various control signals which may be communicated to the one or more UV disinfection devices 102.

Each of the primary UV disinfection device 102A, the auxiliary UV disinfection device 102B, and the mobile control unit 104 may be powered by an external power source 182, such as, for example, alternating current (AC). In certain optional embodiments, the mobile control unit 104 may further include a power source 119, such as, for example, one or more batteries. In certain optional embodiments, the power source 119 may be charged by plugging the mobile control unit 104 into an external power source 182. In other optional embodiments, the power source 119 may be charged by the primary UV disinfection device 102A when the mobile control unit 104 is docked with the primary UV disinfection device 102A and the primary UV disinfection device 102A is plugged in. The external power source 182 may generally be limited to a twenty (20) ampere service.

It may be a primary objective of the disinfection system 100 is reduce a total disinfection cycle time from deployment of at least one of the one or more UV disinfection devices 102 to completion of a disinfection cycle 190. Further, because the total amount of power which may be utilized by the one or more UV disinfection devices 102 is typically limited by the external power source 182, it may be another objective of the disinfection system 100 to efficiently and effectively allocate power between each of the plurality of UV emitters 130 and reduce a treatment time to complete a disinfection cycle 190. A further objective of the disinfection system 100 may be, regardless of a positioned of the primary UV disinfection device 102A with the area 10 to optimally align the plurality of UV emitters 130 within the area 10 to reduce the treatment time to complete the disinfection cycle 190.

The control system, via one or more of the controllers 106, 160, may be configured to control the power state of the at least one of the one or more UV disinfection devices 102. In certain optional embodiments, the control system, via one or more of the controllers 106, 160, may be configured to identify when power (e.g., from an external power source 182) is applied to the one or more UV disinfection devices 102.

The control system, via one or more of the controllers 106, 160, may further be configured to automatically activate the auxiliary amalgam heating assembly 150 to heat the amalgam spot 134 of each of the plurality of UV emitters 130 in response to the power state 180. In certain optional embodiments, the auxiliary amalgam heating assembly 150 may be automatically activated when power is applied to a corresponding one of the one or more UV disinfection devices 102. The auxiliary amalgam heating assembly 150 may operate independently of the at least one ballast 138 of the plurality of UV emitters 130. By automatically activating the auxiliary amalgam heating assembly 150, a preheating time of each of the plurality of UV emitters 130 may be reduced as the auxiliary amalgam heating assembly 150 is activated before the plurality of UV emitters 130 are activated. Due to the preheating provided by the auxiliary amalgam heating assembly 150, a total disinfection cycle time may be reduced.

The control system, via one or more of the controllers 106, 160, may further be configured to selectively activate the plurality of UV emitters 130, independent of the activation of the auxiliary amalgam heating assembly 150.

The control system, via one or more of the controllers 106, 160, may further be configured to begin a disinfection cycle 190 once a ballast current of the plurality of UV emitters 130 has stabilized.

The control system, via one or more of the controllers 106, 160, may further be configured to determine whether a predetermined disinfection dose (e.g., of UV light 101 or energy) is achieved by each of the plurality of UV sensors 140. The predetermined disinfection dose may be based in part the reflected irradiance value of each of the plurality of UV sensors 140 and an elapsed time since beginning the disinfection cycle 190. The predetermined disinfection dose may also be referred to herein as a germicidal dose, a bactericidal dose, or the like.

The control system, via one or more of the controllers 106, 160, may further be configured to complete the disinfection cycle 190 and deactivate the auxiliary amalgam heating assembly 150 once each of the plurality of UV sensors 140 has achieved the predetermined disinfection dose.

In certain optional embodiments, the control system, via one or more of the controllers 106, 160, may further be configured to: increase an applied power-level to at least one of the plurality of heating elements when a temperature of the amalgam spot 134 of at least one of the plurality of UV emitters 130 is below a predetermined optimal operating temperature; and decrease the applied power-level to at least one of the plurality of heating elements when the temperature is above the predetermined optimal operating temperature. The temperature may be monitored by one or more of the controller 160 or the auxiliary amalgam heating assembly 150.

In certain optional embodiments, the control system, via one or more of the controllers 106, 160, may further be configured to simultaneously control an applied power-level to each of the plurality of heating elements 152 of the auxiliary amalgam heating assembly 150.

In certain optional embodiments, the control system, via one or more of the controllers 106, 160, may further be configured to maximize a sensed reflected irradiance value of each of the plurality of UV sensors 140 by dynamically varying a power-level of corresponding emitters of the plurality of UV emitters 130.

In certain optional embodiments, the control system, via one or more of the controllers 106, 160, may further be configured to: measure an initial reflected irradiance value by each of the plurality of UV sensors 140 associated with a maximum power-level of each of the plurality of UV emitters 130; reduce a power-level of each of the plurality of UV emitters 130 by a predetermined percentage of the maximum power-level; identify a lowest initial value of the initial reflected irradiance values associated with a lowest sensor of the plurality of UV sensors 140; maximize a sensed reflected irradiance value of the lowest sensor by increasing the power-level of a corresponding one the plurality of UV emitters 130 associated with the lowest sensor of the plurality of UV sensors 140; define a target reflected irradiance value corresponding to the maximized sensed reflected irradiance value of the lowest sensor.

In certain optional embodiments, the control system, via one or more of the controllers 106, 160, may further be configured to sequentially increase the power-level of remaining ones of the plurality of UV emitters 130 associated with each of the plurality of UV sensors 140 beginning with an emitters of the plurality of UV emitters 130 associated with a next lowest initial value of the initial reflected irradiance values until each associated sensed reflected irradiance value is greater than or equal to the target reflected irradiance value.

In certain optional embodiments, the control system, via one or more of the controllers 106, 160, may further be configured to, prior to maximizing the sensed reflected irradiance value of each of the plurality of UV sensors 140, rotate the emitter array 132 to an optimal array position based at least in part on initial reflected irradiance values measured by each of the plurality of UV sensors 140 at different positions of the sensor array 142. The control system may be configured to rotate the emitter array 132 and the sensor array 142 in unison. The different positions of the sensor array 142 may be rotationally offset from each other.

In certain optional embodiments, the control system, via one or more of the controllers 106, 160, may further be configured to selectively deactivate each of the plurality of UV emitters 130 and a corresponding sensor of the plurality of UV sensors 140 in response to the corresponding sensor of the plurality of UV sensors 140 achieving the predetermined disinfecting dose.

In certain optional embodiments, the control system, via one or more of the controllers 106, 160, may further be configured to dynamically vary a power-level of remaining active emitters of the plurality of UV emitters 130 and sensing reflected irradiance values corresponding to the varied power-level for maximizing the sensed reflected irradiance values in order of priority from lowest to highest sensed reflected irradiance values of remaining active sensors of the plurality of UV sensors 140.

The terms "controller," "control circuit" and "control circuitry" as used herein may refer to, be embodied by or otherwise included within a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed and programmed to perform or cause the performance of the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The term "computer-readable memory medium" as used herein may refer to any non-transitory medium 112, 164 alone or as one of a plurality of non-transitory memory media 112, 164 within which is embodied in a computer program product 118, 172 that includes processor-executable software, instructions or program modules which upon execution may provide data or otherwise cause a computer system to implement subject matter or otherwise operate in a specific manner as further defined herein. It may further be understood that more than one type of memory media may be used in combination to conduct processor-executable software, instructions or program modules from a first memory medium upon which the software, instructions or program modules initially reside to a processor for execution.

"Memory media" as generally used herein may further include without limitation transmission media and/or storage media. "Storage media" may refer in an equivalent manner to volatile and non-volatile, removable and non-removable media, including at least dynamic memory, application specific integrated circuits (ASIC), chip memory devices, optical or magnetic disk memory devices, flash memory devices, or any other medium which may be used to stored data in a processor-accessible manner, and may unless otherwise stated either reside on a single computing platform or be distributed across a plurality of such platforms. "Transmission media" may include any tangible media effective to permit processor-executable software, instructions or program modules residing on the media to be read and executed by a processor, including without limitation wire, cable, fiber-optic and wireless media such as is known in the art.

The term "processor" as used herein may refer to at least general-purpose or specific-purpose processing devices and/ or logic as may be understood by one of skill in the art, including but not limited to single- or multithreading processors, central processors, parent processors, graphical processors, media processors, and the like.

Referring to FIG. 7, with further illustrative reference back to FIGS. 1A-6, an embodiment of a method 200 may now be described which is exemplary but not limiting on the scope the present disclosure unless otherwise specifically noted. One of skill in the art may appreciate that alternative embodiments may include fewer or additional steps, and that certain disclosed steps may for example be performed in different chronological order or simultaneously. Unless otherwise specifically noted, operations, steps, functions, processes, and the like as disclosed in association with the method 200 may be executed or directed by a single computing device, or via multiple computing devices in operable communication via a communications network. Exemplary such computing devices may include onboard controllers 106, 160 or machine control systems, remote (e.g., cloud) servers, mobile user devices, and the like.

The method 200 may be directed to disinfecting an area 10 or 12 with a predetermined disinfection dose of UV light 101. The method 200 may include step (a) positioning 202 the primary UV disinfection device 102A in the area 10 or 12. The primary UV disinfection device 102A may include a plurality of UV emitters 130 positioned in an emitter array 132 and a plurality of UV sensors 140 positioned in a sensor array 142. Each of the plurality of UV emitters 130 may include an amalgam spot 134 and may be configured to emit UV light 101 (also referred to herein as UV energy 101). Each of the plurality of UV sensors 140 may be configured to measure a reflected irradiance value indirectly from one or more of the plurality of UV emitters 130 via reflection off of one or more surfaces 14 of the area 10 or 12.

The method 200 may further include step (b) applying 204 power to the primary UV disinfection device 102A.

The method 200 may further include step (c) automatically in response to the applied power, activating 206 an auxiliary amalgam heating assembly 150 to heat the amalgam spot 134 of each of the plurality of UV emitters 130.

The method 200 may further include step (d) selectively activating 208 the plurality of UV emitters 130, independent of activating the auxiliary amalgam heating assembly 150.

The method 200 may further include step (e) beginning 210 a disinfection cycle 190 once each of the plurality of UV emitters 130 have warmed up. As further discussed below, generally the plurality of UV emitters 130 will be warmed up once either the ballast current to the plurality of UV emitters 130 has stabilized or a warmup timer has expired.

The method 200 may further include step (f) determining 212 whether the predetermined disinfecting dose is achieved by each of the plurality of UV sensors 140 based at least in part on the reflected irradiance measured by each of the plurality of UV sensors 140 and an elapsed time since beginning the disinfection cycle 190.

The method 200 may further include step (g) completing 214 the disinfection cycle 190 and deactivating the auxiliary amalgam heating assembly 150 once each of the plurality of UV sensors 140 has achieved the predetermined disinfecting dose.

In certain optional embodiments, the step (c) of the method 200 may further comprise: monitoring a temperature of the amalgam spot 134 of at least one of the plurality of UV emitters 130; increasing an applied power-level to the auxiliary amalgam heating assembly 150 when the monitored temperature is below a predetermined optimal emitter temperature; and decreasing the applied power-level to the auxiliary amalgam heating assembly 150 when the monitored temperature is above the predetermined optimal emitter temperature.

In other optional embodiments, the step (c) of the method 200 may further comprise controlling an applied power-level to a plurality of heating elements 152 of the auxiliary amalgam heating assembly 150 simultaneously.

In further optional embodiments, the step (e) of the method 200 may further comprise maximizing a sensed reflected irradiance value of each of the plurality of UV sensors 140 by dynamically varying a power-level of each of the plurality of UV emitters 130.

In certain optional embodiments, the method 200 may further comprise: measuring an initial reflected irradiance value by each of the plurality of UV sensors 140 associated with a maximum power-level of each of the plurality of UV emitters 130; reducing a power-level of each of the plurality of UV emitters 130 by a predetermined percentage of the maximum power-level; identifying a lowest initial value of the initial reflected irradiance values associated with a lowest sensor of the plurality of UV sensors 140; maximizing the sensed reflected irradiance value of the lowest sensor by increasing the power-level of a corresponding one the plurality of UV emitters 130 associated with the lowest sensor of the plurality of UV sensors 140; and defining a target reflected irradiance value corresponding to the maximized sensed reflected irradiance value of the lowest sensor.

In other optional embodiments, the method 200 may further comprise increasing the power-level of two of the plurality of UV emitters 130 adjacent to the corresponding one of the plurality of UV emitters 130 associated with the lowest sensor of the plurality of UV sensors 140 prior to defining the target reflected irradiance value.

In further optional embodiments, the method 200 may further comprise sequentially increasing the power-level of remaining ones of the plurality of UV emitters 130 beginning with a next lowest initial value of the initial reflected irradiance values until each of the sensed reflected irradiance values is greater than or equal to the target reflected irradiance value.

In certain optional embodiments, the method 200 may further comprise: identifying one or more of the plurality of UV sensors 140 with an associated sensed reflected irradiance value less than the target reflected irradiance value; and activating one or more additional UV emitters 130A to increase the associated sensed reflected irradiance values of the one or more of the plurality of UV sensors 140 to be greater than or equal to the target reflected irradiance value.

In other optional embodiments, prior to maximizing the sensed reflected irradiance value of each of the plurality of UV sensors, the method 200 may further comprise rotating the emitter array 132 to an optimal array position based at least in part on initial reflected irradiance values measured by each of the plurality of UV sensors 140 at different positions of the sensor array 142. The different positions may be rotationally offset from each other so as to enable the reflective irradiance to be captured with a high resolution over a three-hundred-sixty (360) degree field of view.

In certain further optional embodiments, step (g) of the method 200 may further comprise selectively deactivating each of the plurality of UV emitters 130 and a corresponding sensor of the plurality of UV sensors 140 in response to the corresponding sensor achieving the predetermined disinfecting dose.

In further optional embodiments, the method 200 may further comprise dynamically varying a power-level of remaining active emitters of the plurality of UV emitters 130 and sensing reflected irradiance values corresponding to the varied power-level for maximizing the sensed reflected irradiance values in order of priority from lowest to highest of the sensed reflected irradiance values of remaining active sensors of the plurality of UV sensors 140.

Figure 8:
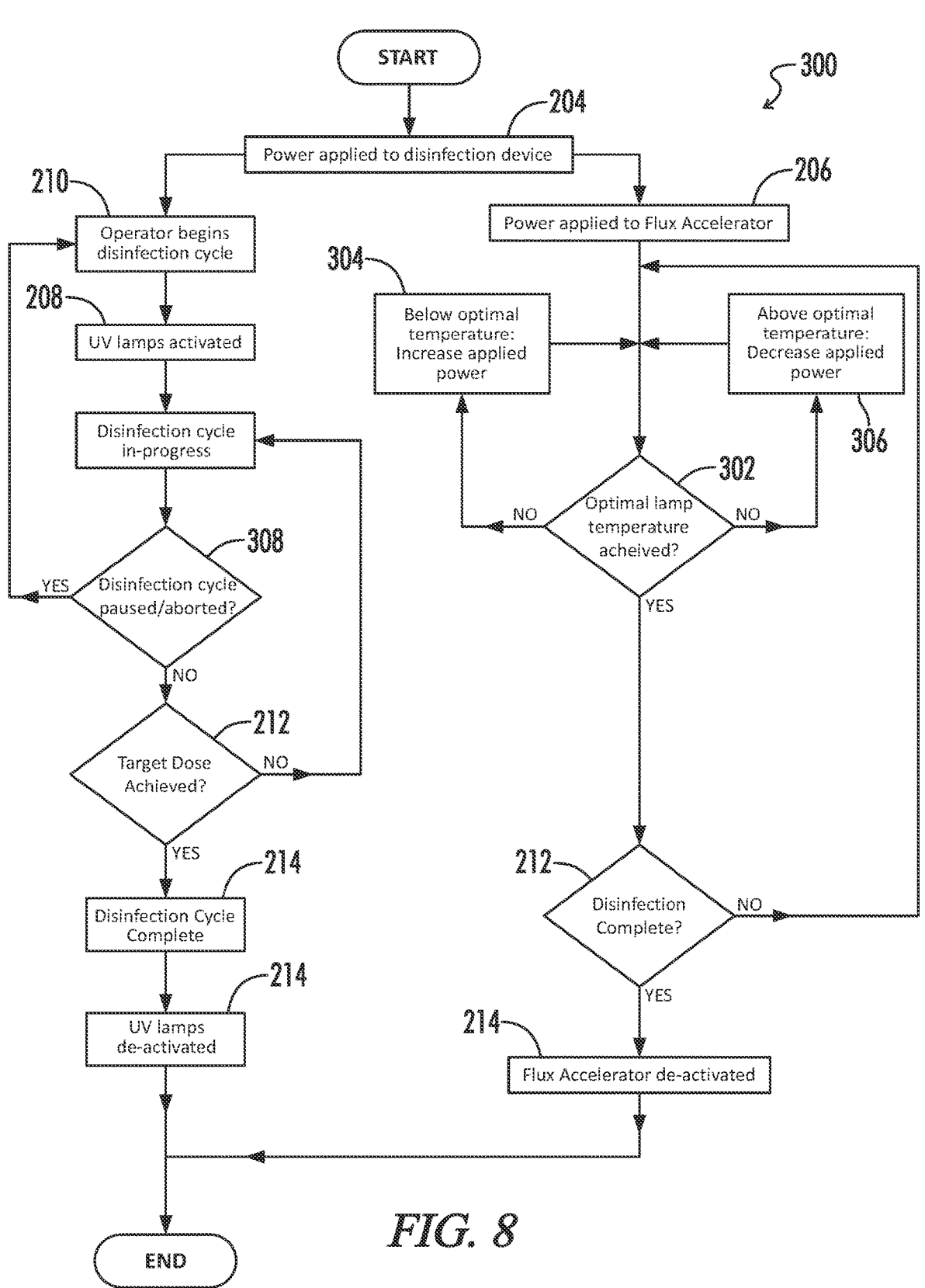
FIG. 8 is a flowchart containing optional method steps in accordance with the flowchart of FIG. 7 in accordance with the present disclosure.

Referring to FIG. 8, an optional method step flowchart 300 illustrating additional optional details of the method 200 is provided. The optional method step flowchart 300 may include each of steps (b), (c), (d), (e), and (f). In certain optional embodiments, and as illustrated, the step of activating 208 the plurality of UV emitters 130 (e.g., step (d)) may occur prior to the step of beginning 210 the disinfection cycle 190 (e.g., step (e)). In this way, it may be more clearly understood how the total disinfection cycle time, which may begin upon beginning the disinfection cycle 190, is reduced by reducing the time necessary to warm up the plurality of UV emitters 130 by using the auxiliary amalgam heating assembly 150. In other optional embodiments, the total disinfection cycle time may begin upon deployment (e.g., step (a) positioning 202) of the one or more UV disinfection devices 102 in the area 10 or 12.

In certain optional embodiments, the optional method step flowchart 300 may further include, following the step of activating 206 an auxiliary amalgam heating assembly 150, monitoring 302 a temperature of the amalgam spot 134 of at least one of the plurality of UV emitters 130; increasing 304 an applied power-level to the auxiliary amalgam heating assembly 150 when the monitored temperature is below a predetermined optimal emitter temperature; and decreasing 306 the applied power-level to the auxiliary amalgam heating assembly 150 when the monitored temperature is above the predetermined optimal emitter temperature.

In other optional embodiments, the optional method step flowchart 300 may further include, while the disinfection cycle 190 is in progress, pausing/aborting 308 the disinfection cycle 190 and then potentially restarting it.

Figure 9:
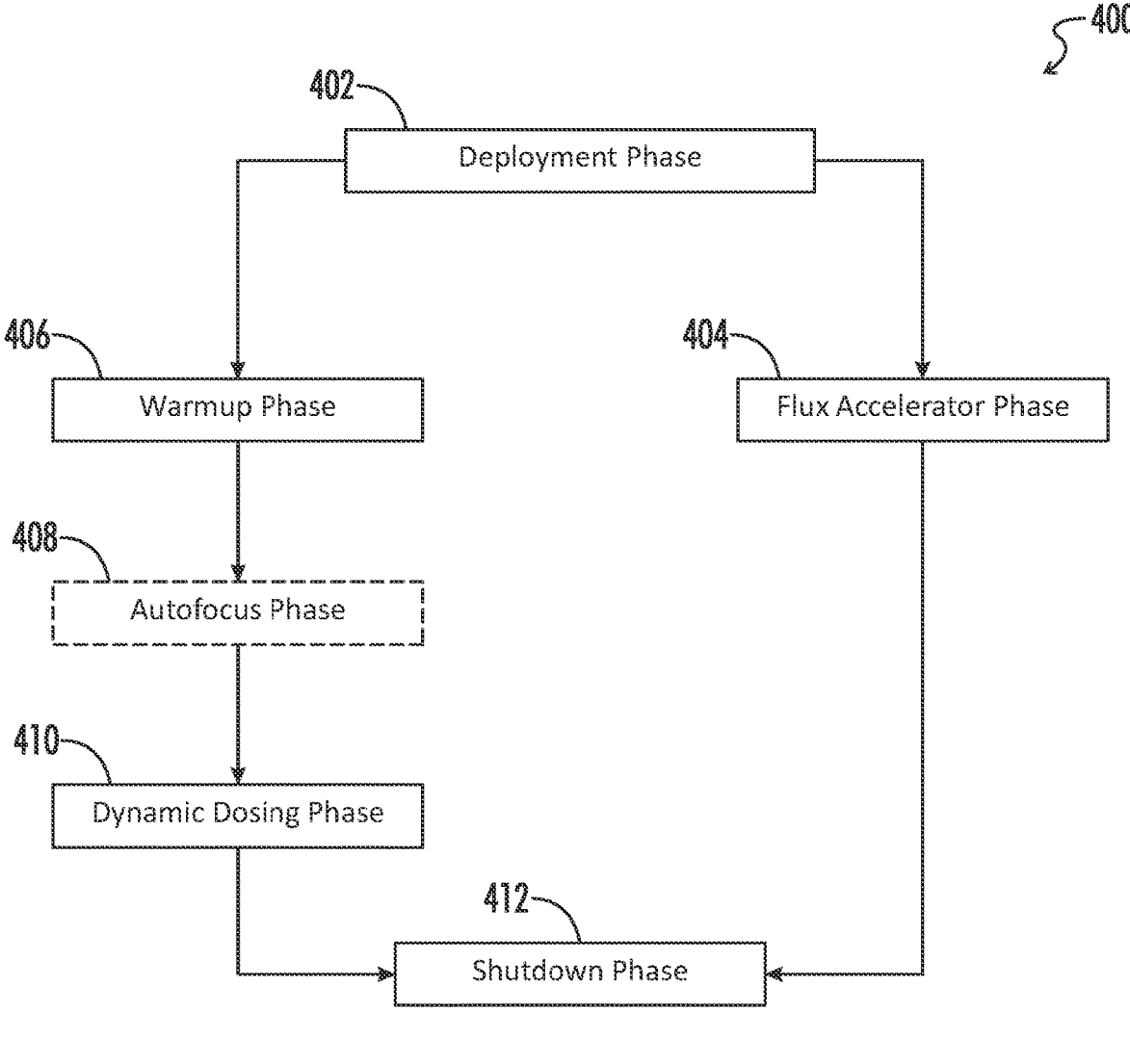
FIG. 9 is a flowchart of another embodiment of a method of disinfecting an area with a predetermined disinfection dose of UV energy in accordance with the present disclosure.

Referring to FIG. 9, with further illustrative reference back to FIGS. 1A-6, an embodiment of a method 400 may now be described which is exemplary but not limiting on the scope the present disclosure unless otherwise specifically noted. One of skill in the art may appreciate that alternative embodiments may include fewer or additional steps, and that certain disclosed steps may for example be performed in different chronological order or simultaneously. Unless otherwise specifically noted, operations, steps, functions, processes, and the like as disclosed in association with the method 400 may be executed or directed by a single computing device, or via multiple computing devices in operable communication via a communications network. Exemplary such computing devices may include onboard controllers 106, 160 or machine control systems, remote (e.g., cloud) servers, mobile user devices, and the like.

The method 400 may be directed to disinfecting an area 10 or 12 with a predetermined disinfection dose of UV light 101. The method 400 may include a deployment phase 402. The deployment phase 402 may include step (a) selectively positioning the primary UV disinfection device 102A in the area 10. As discussed above, the primary UV disinfection device 102A may include a plurality of UV emitters 130 positioned in a circumferential emitter array 132 and a plurality of UV sensors 140 positioned in a circumferential sensor array 142. Each of the plurality of UV emitters 130 may be configured to emit UV light 101. The deployment phase 402 may include applying power to the UV disinfection device 102A. This is similar to step (b) of the method 200.

The method 400 may further include flux accelerator phase 404. The flux accelerator phase 404 may include, automatically in response to the applied power, activating the auxiliary amalgam heating assembly 150 to heat the amalgam spot 134 of each of the plurality of UV emitters 130. This is similar to step (c) of the method 200.

The method 400 may further include a warmup phase 406. The warmup phase 406 may include selectively activating the plurality of UV emitters 130 independent of the activating of the auxiliary amalgam heating assembly 150. This is similar to step (d) of the method 200.

The method 400 may further include an autofocus phase 408. The autofocus phase 408 may include step (b) measuring a plurality of initial reflected irradiance values by each of the plurality of UV sensors 140 corresponding to a plurality of array positions of the circumferential sensor array 142. The plurality of array positions may be rotationally offset. In certain optional embodiments, the both the circumferential sensor array 142 and the circumferential emitter array 132 may rotated in unison to each of the plurality of array positions. In other optional embodiments, the circumferential sensor array 142 may rotationally move to each of the plurality of array positions while the circumferential emitter array 132 remains stationary.

The autofocus phase 408 may further include step (c) rotating the circumferential emitter array 132 to an optimal array position. The optimal array position may be determined at least in part on at least one of the measured plurality of initial reflected irradiance values of the plurality of UV sensors 140.

The autofocus phase 408 may further include step (d) measuring an optimal position initial reflected irradiance value by each of the plurality of UV sensors 140 corresponding to the optimal array position. In certain optional embodiments, step (d) may be performed with each of the plurality of UV emitters 130 set a maximum power level.

The autofocus phase 408 may include comparing each of the plurality of initial reflected irradiance values measured by each of the plurality of UV sensors 140 corresponding to each of the plurality of array positions of the circumferential sensor array 142, and determining the optimal array position of the circumferential emitter array 132 as at one of the plurality of array positions or between any two of the plurality of array positions.

In certain optional embodiments, the step of determining the optimal array position of the autofocus phase 408 may further comprise: identifying a lowest measured minimum value of the plurality of initial reflected irradiance values of the plurality of UV sensors 140 corresponding to a lowest minimum array position of the plurality array positions; and defining the optimal array position as the lowest minimum array position. This optional method step may depend upon the efficacy impact of rotating the plurality of UV sensors 140. If efficacy varies greatly with sensor rotation, then the plurality of UV sensors 140 may be placed in a non-optimal position. This may be similar to the current method of operation which uses the lowest sensor to determine the total disinfection cycle time. By rotating sensors to find the lowest of the lows (e.g., the lowest measured minimum value), adequate disinfection in the entire treatment area may be guaranteed.

In other optional embodiments, the step of determining the optimal array position of the autofocus phase 408 may further comprise: identifying a lowest measured minimum value of the plurality of initial reflected irradiance values corresponding to one of the plurality of array positions; identifying a highest measured minimum value of the plurality of initial reflected irradiance values corresponding to a different one of the plurality of array positions; identifying a midpoint array position of the plurality of array positions wherein each of the plurality of initial reflected irradiance values of the plurality of UV sensors 140 corresponding to the midpoint array position is greater than or equal to an average between the lowest measured minimum value and the highest measured minimum value of the plurality of initial reflected irradiance values of the plurality of UV sensors 140; and defining the optimal array position as the identified midpoint array position. This optional method step may depend upon the efficacy impact of rotating the plurality of UV sensors 140. If efficacy varies minimally with sensor rotation, then the plurality of UV sensors 140 may be rotated such that the lowest sensor value represents a mid-point between the highest measured minimum value (e.g., optimal reading) and the lowest measured minimum value (non-optimal reading). This position may seek to reduce the total disinfection cycle time while minimizing impacts to efficacy.

In further optional embodiments, the step of determining the optimal array position of the autofocus phase 408 may further comprise: identifying a highest measured minimum value of the plurality of initial reflected irradiance values corresponding to a highest minimum array position the plurality of array positions; and defining the optimal array position as the highest minimum array position. This optional method step may depend upon the efficacy impact of rotating the plurality of UV sensors 140. If sensor rotation has no impact on efficacy, then the plurality of UV sensors 140 may be rotated in such a way to maximize the reading from the lowest sensor (e.g., the highest measured minimum value). This may reduce the total disinfection cycle time as much as possible without manually repositioning the device.

The method 400 may further include a dynamic dosing phase 410. The dynamic dosing phase 410 may occur without the autofocus phase 408. The dynamic dosing phase 410 may include step (e) dynamically varying a power-level of each of the plurality of UV emitters 130 and sensing reflected irradiance values corresponding to the varied power-level for maximizing the sensed reflected irradiance values in order of priority from lowest to highest of the measured optimal position initial reflected irradiance values of the plurality of UV sensors 140.

The dynamic dosing phase 410 may further include step (f) beginning a disinfection cycle 190 and recording a total accumulated UV irradiance by each of the plurality of UV sensors 140. The total accumulated UV irradiance may depend at least in part on the sensed reflected irradiance value of each of the plurality of UV sensors 140 and an elapsed time since beginning the disinfection cycle 190. As such, the dynamic dosing phase 412 includes steps similar to steps (e) and (f) of the method 200.

The method 400 may further include a shutdown phase 412. The shutdown phase 414 may include step (g) completing the disinfection cycle 190 once the total accumulated UV irradiance of each of the plurality of UV sensors 140 is greater than or equal to the predetermined disinfection dose. The shutdown phase 412 may further include deactivating the auxiliary amalgam heating assembly 150. The shutdown phase 414 is similar to step (g) of the method 200.

In certain optional embodiments, steps (b) and (c) of the method 400 may further include simultaneously moving the circumferential emitter array 132 and the circumferential sensor array 142.

In further optional embodiments, the method 400 may further comprise, prior to step (b), warming-up the plurality of UV emitters 130 until a ballast current of each of the plurality of UV emitters 130 is stabilized.

In other optional embodiments, the method 400 may further comprise, prior to step (c), comparing each of the plurality of initial reflected irradiance values measured by each of the plurality of UV sensors 140 corresponding to each of the plurality of array positions of the circumferential sensor array 142, and determining the optimal array position of the circumferential emitter array 132 as at one of the plurality of array positions or between any two of the plurality of array positions.

In certain optional embodiments, the step of determining the optimal array position of the method 400 may further comprise: identifying a lowest measured minimum value of the plurality of initial reflected irradiance values of the plurality of UV sensors 140 corresponding to a lowest minimum array position of the plurality array positions; and defining the optimal array position as the lowest minimum array position. This optional method step may depend upon the efficacy impact of rotating the plurality of UV sensors 140. If efficacy varies greatly with sensor rotation, then the plurality of UV sensors 140 may be placed in a non-optimal position. This may be similar to the current method of operation which uses the lowest sensor to determine the total disinfection cycle time. By rotating sensors to find the lowest of the lows (e.g., the lowest measured minimum value), adequate disinfection in the entire treatment area may be guaranteed.

In other optional embodiments, the step of determining the optimal array position of the method 400 may further comprise: identifying a lowest measured minimum value of the plurality of initial reflected irradiance values corresponding to one of the plurality of array positions; identifying a highest measured minimum value of the plurality of initial reflected irradiance values corresponding to a different one of the plurality of array positions; identifying a midpoint array position of the plurality of array positions wherein each of the plurality of initial reflected irradiance values of the plurality of UV sensors 140 corresponding to the midpoint array position is greater than or equal to an average between the lowest measured minimum value and the highest measured minimum value of the plurality of initial reflected irradiance values of the plurality of UV sensors 140; and defining the optimal array position as the identified midpoint array position. This optional method step may depend upon the efficacy impact of rotating the plurality of UV sensors 140. If efficacy varies minimally with sensor rotation, then the plurality of UV sensors 140 may be rotated such that the lowest sensor value represents a mid-point between the highest measured minimum value (e.g., optimal reading) and the lowest measured minimum value (non-optimal reading). This position may seek to reduce the total disinfection cycle time while minimizing impacts to efficacy.

In further optional embodiments, the step of determining the optimal array position of the method 400 may further comprise: identifying a highest measured minimum value of the plurality of initial reflected irradiance values corresponding to a highest minimum array position the plurality of array positions; and defining the optimal array position as the highest minimum array position. This optional method step may depend upon the efficacy impact of rotating the plurality of UV sensors 140. If sensor rotation has no impact on efficacy, then the plurality of UV sensors 140 may be rotated in such a way to maximize the reading from the lowest sensor (e.g., the highest measured minimum value). This may reduce the total disinfection cycle time as much as possible without manually repositioning the device.

In certain optional embodiments, step (e) of the method 400 may further comprise: reducing the power-level of each of the plurality of UV emitters by a predetermined percentage; identifying a lowest initial value of the optimal position initial reflected irradiance values associated with a lowest sensor of the plurality of UV sensors 140; maximizing the sensed reflected irradiance value of the lowest sensor by increasing the power-level of a corresponding one the plurality of UV emitters 130 associated with the lowest sensor of the plurality of UV sensors 140; and defining a target reflected irradiance value corresponding to the maximized sensed reflected irradiance value of the lowest sensor.

In other optional embodiments, the method 400 may further comprise increasing the power-level of two of the plurality of UV emitters 130 adjacent to the corresponding one of the plurality of UV emitters associated with the lowest sensor of the plurality of UV sensors 140 prior to defining the target reflected irradiance value.

In further optional embodiments, the method 400 may further comprise sequentially increasing the power-level of remaining ones of the plurality of UV emitters 130 beginning with a next lowest initial value of the optimal position initial reflected irradiance values until each of the sensed reflected irradiance values is greater than or equal to the target reflected irradiance value.

In still further optional embodiments, the method 400 may further comprise activating one or more additional UV emitters 130A (shown in FIG. 3B) to increase the sensed reflected irradiance values of each of the plurality of UV sensors 140 to be greater than or equal to the target reflected irradiance value. In certain optional embodiments, the one or more additional UV emitters 130A may be positioned between or next to each of the plurality of UV emitters 130. In other optional embodiments, the one or more additional UV emitters 130A may be positioned between selected ones of the plurality of UV emitters 130.

In other optional embodiments, step (g) of the method 400 may further comprise selectively deactivating each of the plurality of UV emitters 130 once the total accumulated UV irradiance of a corresponding sensor of the plurality of UV sensors 140 is greater than or equal to the predetermined disinfection dose.

In further optional embodiments, the method 400 may further comprise dynamically varying the power-level of remaining active emitters of the plurality of UV emitters 130 for maximizing the sensed reflected irradiance values in order of priority from lowest to highest of the sensed reflected irradiance values of certain ones of the plurality of UV sensors 140 associated with the remaining active emitters.

The various phases of the method 400 may generally be described as follows. During the deployment phase 402, the operator is instructed to setup the one or more UV disinfection devices 102 and prepare the room for optimal disinfection. When the device is first energized by plugging into an available wall outlet, the auxiliary amalgam heating assembly 150 is automatically activated and remains active until device shut down (e.g., the flux accelerator phase 404). Upon leaving the room, the operator secures all entryways then enters operator credentials in the remote. The operator is then asked to confirm that the room is secure and that they are safely positioned outside the room. Upon confirmation, a warmup phase 406 begins.

Upon commencement of the warmup phase 406, the plurality of UV emitters 130 are activated and begin to approach maximum operational capacity. Because the plurality of UV emitters 130 are active, the in-room motion detection system is also activated at this time. The device uses a warm-up timer and emitter-power feedback (e.g., monitors the ballast current) to determine when the warm-up phase is complete. Once complete, the system will automatically proceed to the autofocus phase 408. Remote setup procedures may or may not be complete at this time.

During the autofocus phase 408, the primary UV disinfection device 102A rotates the emitter and sensor array to capture reflected irradiance measurements at each UV sensor in at least two (2) array positions. By obtaining measurements in multiple array positions, reflected irradiance will be captured with high resolution over a 360° field of view. The system then compares the irradiance measurements captured by each UV sensor in each array position, returning the emitter and sensor array to an optimal position for completing the disinfection cycle 190. Once the emitter and UV sensor array reaches the optimal position, the dynamic dosing phase 410 begins. Remote setup procedures may or may not be complete during this phase, but must be completed before proceeding to the next phase.

Upon commencement of the dynamic dosing phase 410, the system begins to vary the power-level of emitters activated during the warmup phase 406. While emitter power is varied, the system analyses the resulting impact to measured irradiance values at each UV sensor. The cycle time impact of each UV sensor is determined, relative to measured irradiance values, and the system determines the appropriate order in which each UV sensors will be targeted to achieve the required disinfecting dose. Sensors which measure the lowest levels of reflected irradiance during the analysis period will be targeted to achieve the required dose first, while sensors measuring a higher level of reflected irradiance will be targeted last. As a result, varying emitter power to maximize the measured irradiance of each UV sensor, in order from lowest initial value to highest initial value, the system achieves the fastest allowable cycle time under limited power availability from a standard wall outlet. The disinfection cycle 190 begins during this phase.

During the shutdown phase 412, when the last UV sensor within the array of UV sensors achieves the required dose, the disinfection cycle 190 is complete. The auxiliary amalgam heating assembly 150 and all active emitters may now be deactivated. The operator is alerted of a completed cycle and all cycle statistics and device diagnostic data may further be transmitted to a central database.

Figure 10:
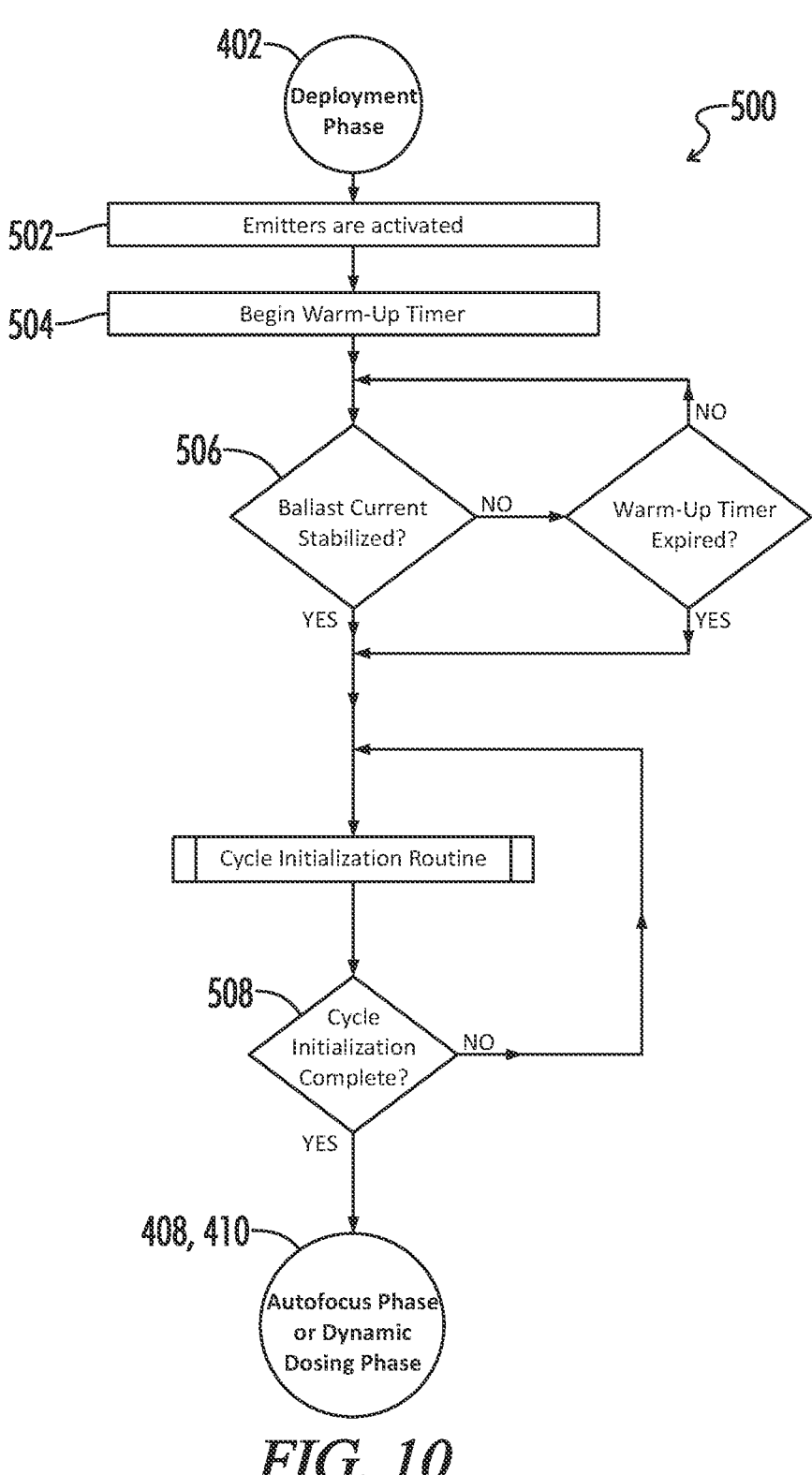
FIG. 10 is a flowchart containing additional optional warmup phase details of the method shown in the flowchart of FIG. 9 in accordance with the present disclosure.

Referring to FIG. 10, a detailed warmup phase flowchart 500 illustrating additional optional details of the warmup phase 406 of the method 400 is provided. In certain optional embodiments, the warmup phase 406 further include activating 502 the plurality of UV emitters 130, while the one or more additional UV emitters 130A remain inactive. In other optional embodiments, the warmup phase 406 may further include beginning 504 a warm-up timer and monitoring 506 the ballast current. Once either the ballast current has stabilized or the warm-up timer has expired, the warmup phase 406 may further include confirming 508 whether a cycle initialization routine is complete. In certain optional embodiment, the warmup phase 406 may further include determining whether a remote setup is confirmed and/or confirming whether a door monitor is active. The remote setup may referred to a setup of the mobile control unit 104. The step of determining whether the remote setup is confirmed may in an embodiment optionally include confirming whether a door monitor is active and further confirming whether a cycle initialization is complete.

Figure 11B:
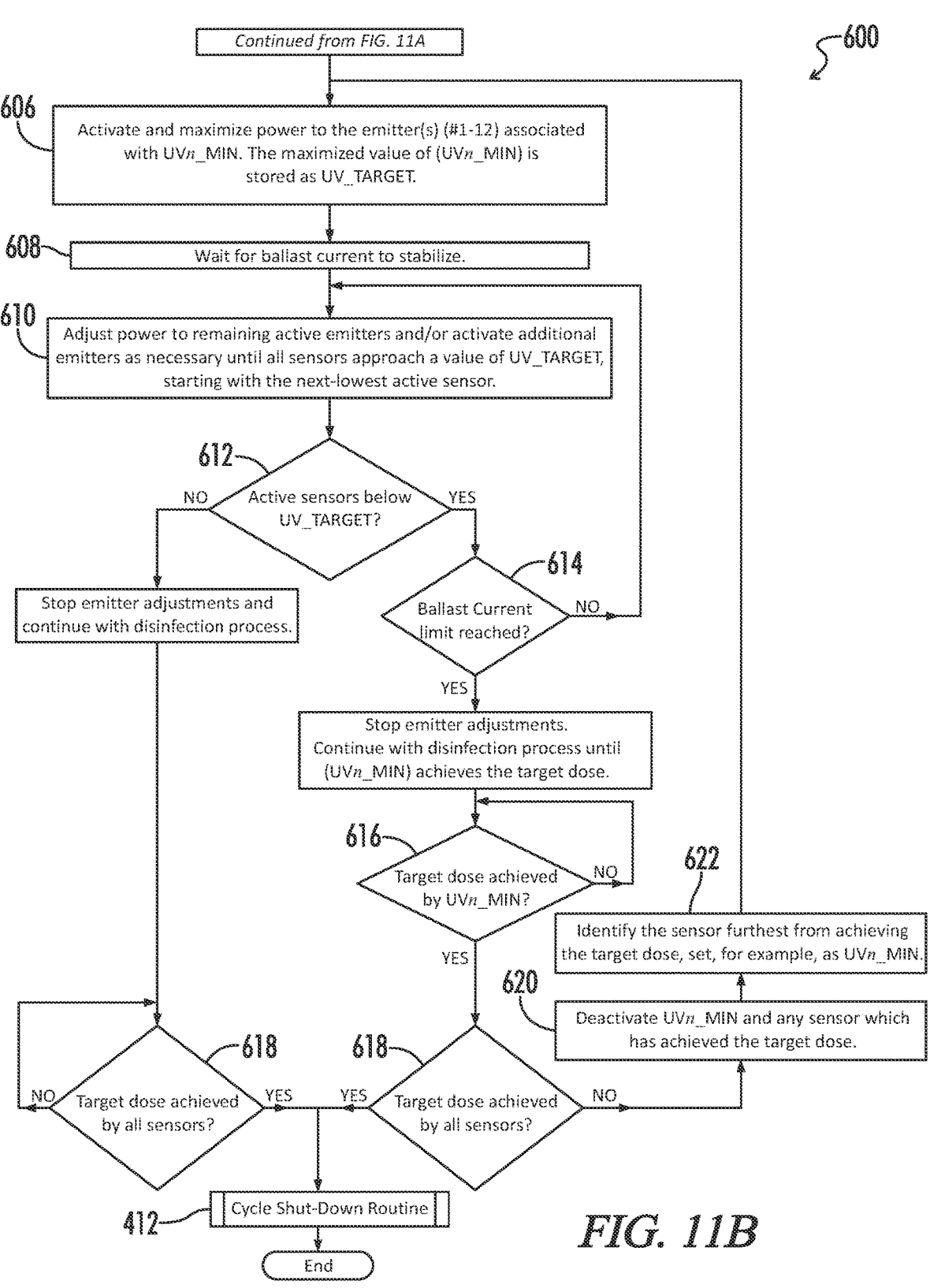
FIG. 11B is a continuation of the flowchart of FIG. 11A in accordance with the present disclosure.

Referring to FIGS. 11A-11B, a detailed dynamic dosing flowchart 600 illustrating additional optional details of the dynamic dosing phase of the method 400 is provided. In certain optional embodiments, determining 510 whether the remote setup is confirmed may be performed during any of steps (d), (e), (f), or (g) of the method 400.

In certain optional embodiments, step (d) of the method 400 may further include calculating 601 an average reflected irradiance of optimal position initial reflected irradiance values of the plurality of UV sensors and identifying a lowest optimal sensor associated with a lowest optimal position reflected irradiance value. The step of calculating 601 may be performed with the plurality of UV emitters 130 at a maximum power-level or at a predetermined percentage, such as, for example be approximately 50% of the maximum power level. The method 400 may further include calculating 602 an estimated total disinfection cycle time by dividing the predetermined disinfection dose by the average reflected irradiance. The method 400 may further include transmitting the estimated total disinfection cycle time to the mobile control unit 104.

In certain optional embodiments, such as when the step of calculating is performed at maximum power-level, the detailed dynamic dosing flowchart 600 may include reducing the power-level of each of the plurality of UV emitters 130 by the predetermined percentage. The predetermined percentage may for example be approximately 50% of the maximum power level. Following the reducing step, the method 400 may further include maximizing 606 a power-level of one of the plurality of UV emitters 130 associated with the lowest optimal sensor, while also activating and/or maximizing a power-level of two emitters adjacent thereto. The two emitters may either be of the plurality of UV emitters 130 or of the one or more additional UV emitters 130A. A maximized value of the lowest optimal sensor may be stored as a target reflected irradiance value. Following the maximizing 606 step, the method 400 may include waiting 608 for the ballast current to stabilize.

In certain optional embodiments, the method 400 may further include adjusting 610 a power level to remaining active emitters of the plurality of UV emitters 130 and/or activating one or more additional UV emitters 130A, as necessary, until the sensed reflected irradiance value of each of the plurality of UV sensors 140 approaches (e.g., is greater than or equal to) the target reflected irradiance value. This step may be sequentially performed based upon a next lowest sensor of the plurality of UV sensors 140.

As illustrated by the detailed dynamic dosing flowchart 600 in FIG. 11B, the method 400 may optionally further include determining 612 whether any of the plurality of sensors 140 is below the target reflected irradiance value. If none of the plurality of UV sensors 140 is below the target reflected irradiance value, then the method 400 may proceed with step (f) (e.g., beginning 613 the disinfection cycle 190) until the predetermined disinfection dose has been achieved by all of the plurality of UV sensors 140. If any of the plurality of UV sensors 140 is below the target reflected irradiance value, then the method 400 may further include determining 614 whether a maximum allowable ballast current has been reached. The maximum allowable ballast current may depend upon a total available power supply provided by the external power source 182. If the maximum allowable ballast current has not been reached, then the method 400 will revert back to continuing adjusting 610 the power level to certain active emitters of the plurality of UV emitters 130 associated with any of the plurality of UV sensors 140 measuring below the target reflected irradiance value.

If the maximum allowable ballast current has been reached, then the method 400 may proceed with step (f) (e.g., beginning 613 the disinfection cycle 190) until the predetermined disinfection dose. In certain optional embodiments, at least point, the method 400 may further include determining 616 whether the predetermined disinfection dose has been achieved by the lowest optimal sensor and further determining 618 whether the predetermined disinfection dose has been achieved by all of the plurality of UV sensors 140.

If the predetermined disinfection dose has not been achieved by all of the plurality of UV sensors 140, then the method 400 may further include deactivating 620 any of the plurality of UV sensors 140 which have achieved the predetermined disinfection dose. In certain optional embodiments, the step of deactivating 620 may further include deactivating any of the plurality of UV emitters 130 associated with the deactivated UV sensors. Next, the method 400 may optionally include identifying 622 a sensor of the plurality of UV sensors 140 furthest from achieving the predetermined disinfection dose and then proceeding to repeat steps 606, 608, 610, etc. for remaining active UV emitters associated with that sensor and any other remaining active sensors, sequentially from lowest to highest reflected irradiance value.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Although embodiments of the present invention have been described in detail, it will be understood by those skilled in the art that various modifications can be made therein without departing from the spirit and scope of the invention as set forth in the appended claims.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

The previous detailed description has been provided for the purposes of illustration and description. Thus, although there have been described particular embodiments of a new and useful invention, it is not intended that such references be construed as limitations upon the scope of this disclosure except as set forth in the following claims.

What is claimed is:

1. A method of disinfecting an area with a predetermined disinfecting dose of ultraviolet (UV) energy, the method comprising:

(a) positioning an UV disinfection device in the area, the UV disinfection device including a plurality of UV emitters positioned in an emitter array and a plurality of UV sensors positioned in a sensor array, each of the plurality of UV emitters including an amalgam spot and configured to emit UV energy, each of the plurality of UV sensors configured to measure a reflected irradiance indirectly from one or more of the plurality of UV emitters via reflection off of one or more surfaces of the area;

(b) applying power to the UV disinfection device;

(c) automatically in response to the applied power, activating a heating step for the amalgam spots of each of the plurality of UV emitters;

(d) selectively activating the plurality of UV emitters, independent of the activating of the heating step;

(e) beginning a disinfection cycle once the heating step is completed for each of the plurality of UV emitters;

(f) determining whether the predetermined disinfecting dose is achieved by each of the plurality of UV sensors based at least in part on the reflected irradiance measured by each of the plurality of UV sensors and an elapsed time since beginning the disinfection cycle; and (g) completing the disinfecting cycle and deactivating the heating step for the amalgam spots once each of the plurality of UV sensors has achieved the predetermined disinfecting dose.

2. The method of claim 1, wherein step (c) comprises activating a flux accelerator and further:

monitoring a temperature of the amalgam spot of at least one of the plurality of UV emitters;

increasing an applied power-level to the flux accelerator assembly when the monitored temperature is below a predetermined optimal emitter temperature; and decreasing the applied power-level to the flux accelerator assembly when the monitored temperature is above the predetermined optimal emitter temperature.

3. The method of claim 2, wherein step (c) further comprises:

controlling an applied power-level to a plurality of heating elements of the flux accelerator assembly simultaneously.

4. The method of claim 1, wherein step (e) further comprises:

maximizing a sensed reflected irradiance value of each of the plurality of UV sensors by dynamically varying a power-level of each of the plurality of UV emitters.

5. The method of claim 4, further comprising:

measuring an initial reflected irradiance value by each of the plurality of UV sensors associated with a maximum power-level of each of the plurality of UV emitters;

reducing a power-level of each of the plurality of UV emitters by a predetermined percentage of the maximum power-level;

identifying a lowest initial value of the initial reflected irradiance values associated with a lowest sensor of the plurality of UV sensors;

maximizing the sensed reflected irradiance value of the lowest sensor by increasing the power-level of a corresponding one the plurality of UV emitters associated with the lowest sensor of the plurality of UV sensors; and defining a target reflected irradiance value corresponding to the maximized sensed reflected irradiance value of the lowest sensor.

6. The method of claim 5, further comprising:

increasing the power-level of two of the plurality of UV emitters adjacent to the corresponding one of the plurality of UV emitters associated with the lowest sensor of the plurality of UV sensors prior to defining the target reflected irradiance value.

7. The method of claim 5, further comprising:

sequentially increasing the power-level of remaining ones of the plurality of UV emitters beginning with a next lowest initial value of the initial reflected irradiance values until each of the sensed reflected irradiance values is greater than or equal to the target reflected irradiance value.

8. The method of claim 7, further comprising:

identifying one or more of the plurality of UV sensors with an associated sensed reflected irradiance value less than the target reflected irradiance value; and activating one or more additional UV emitters to increase the associated sensed reflected irradiance values of the one or more of the plurality of UV sensors to be greater than or equal to the target reflected irradiance value.

9. The method of claim 4, wherein prior to maximizing the sensed reflected irradiance value of each of the plurality of UV sensors, the method further comprises:

rotating the emitter array to an optimal array position based at least in part on initial reflected irradiance values measured by each of the plurality of UV sensors at different positions of the sensor array, the different positions being rotationally offset.

10. The method of claim 1, wherein step (g) further comprises:

selectively deactivating each of the plurality of UV emitters and a corresponding sensor of the plurality of UV sensors in response to the corresponding sensor achieving the predetermined disinfecting dose.

11. The method of claim 10, further comprising:

dynamically varying a power-level of remaining active emitters of the plurality of UV emitters and sensing reflected irradiance values corresponding to the varied power-level for maximizing the sensed reflected irradiance values in order of priority from lowest to highest of the sensed reflected irradiance values of remaining active sensors of the plurality of UV sensors.

12. A disinfection system for disinfecting an area with a predetermined disinfecting dose of UV energy, the disinfection system comprising:

a mobile ultraviolet (UV) disinfection device including:

a mobile base supported by one or more ground engaging units;

a plurality of UV lamps oriented vertically and positioned in a lamp array, each of the plurality of UV lamps having a lower end and an interior amalgam spot positioned at a predetermined common distance from the lower end, the interior amalgam spot of each of the plurality of lamps facing towards a central axis of the lamp array; and an auxiliary amalgam heating assembly comprising a plurality of heating elements, each of the plurality of heating elements positioned proximate to the amalgam spot of a corresponding one of the plurality of UV lamps;

a plurality of UV sensors configured to generate reflected irradiance data corresponding to reflected irradiance received indirectly from one or more of the plurality of UV lamps via reflection off of one or more surfaces of the area; and a controller linked to receive the data from the plurality of UV sensors and configured to:

control a power state of the UV disinfection device;

automatically activate the auxiliary amalgam heating assembly to heat the amalgam spot of each of the plurality of UV lamps in response to the power state;

selectively activate the plurality of UV lamps, independent of activation of the auxiliary amalgam heating assembly;

begin a disinfection cycle once a ballast current of the plurality of UV lamps has stabilized;

determine whether the predetermined disinfecting dose is achieved by each of the plurality of UV sensors based at least in part on the reflected irradiance measured by each of the plurality of UV sensors and an elapsed time since beginning the disinfection cycle; and complete the disinfecting cycle and deactivate the auxiliary amalgam heating assembly once each of the plurality of UV sensors has achieved the predetermined disinfecting dose.

13. The disinfection system of claim 12, wherein at least one of one of the controller or the auxiliary amalgam heating assembly is configured to:

monitor a temperature of the amalgam spot of at least one of the plurality of UV lamps;

increase an applied power-level to at least one of the plurality of heating elements when the temperature is below a predetermined optimal operating temperature; and decrease the applied power-level to at least one of the plurality of heating elements when the temperature is above the predetermined optimal operating temperature.

14. The disinfection system of claim 12, wherein:

the controller is configured to simultaneously control an applied power-level to each of the plurality of heating elements of the auxiliary amalgam heating assembly.

15. The disinfection system of claim 12, wherein:

the controller is configured to maximize a sensed reflected irradiance value of each of the plurality of UV sensors by dynamically varying a power-level of each of the plurality of UV lamps.

16. The disinfection system of claim 15, wherein:

the controller is configured to:

measure an initial reflected irradiance value by each of the plurality of UV sensors associated with a maximum power-level of corresponding emitters of the plurality of UV emitters;

reduce a power-level of each of the plurality of UV emitters by a predetermined percentage of the maximum power-level;

identify a lowest initial value of the initial reflected irradiance values associated with a lowest sensor of the plurality of UV sensors;

maximize the sensed reflected irradiance value of the lowest sensor by increasing the power-level of a corresponding one the plurality of UV emitters associated with the lowest sensor of the plurality of UV sensors;

define a target reflected irradiance value corresponding to the maximized sensed reflected irradiance value of the lowest sensor; and sequentially increase the power-level of remaining ones of the plurality of UV emitters associated with each of the plurality of UV sensors beginning with an emitters of the plurality of UV emitters associated with a next lowest initial value of the initial reflected irradiance values until each associated sensed reflected irradiance value is greater than or equal to the target reflected irradiance value.

* * * * *